(12) United States Patent
Kallmyer

(10) Patent No.: US 8,676,337 B2
(45) Date of Patent: Mar. 18, 2014

(54) RECHARGE SYSTEM AND METHOD FOR DEEP OR ANGLED DEVICES

(75) Inventor: Todd A. Kallmyer, Tempe, AZ (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 13/477,140

(22) Filed: May 22, 2012

(65) Prior Publication Data

US 2012/0239107 A1 Sep. 20, 2012

Related U.S. Application Data

(63) Continuation of application No. 12/108,051, filed on Apr. 23, 2008, now Pat. No. 8,204,602.

(51) Int. Cl.
*A61N 1/36* (2006.01)

(52) U.S. Cl.
USPC .......... 607/61; 607/1; 607/2; 607/32; 607/33; 607/37; 607/38; 607/115; 607/116; 607/139; 607/142; 607/149

(58) Field of Classification Search
USPC ............... 607/1–2, 32–33, 37–38, 55–57, 61, 607/115, 116, 139, 142, 149
See application file for complete search history.

(56) References Cited

U.S. PATENT DOCUMENTS

| | | | |
|---|---|---|---|
| 4,581,018 A | 4/1986 | Jassawalla et al. | |
| 4,757,804 A | 7/1988 | Griffith et al. | |
| 5,123,898 A | 6/1992 | Liboff et al. | |
| 5,170,784 A | 12/1992 | Ramon et al. | |
| 5,324,316 A | 6/1994 | Schulman et al. | |
| 5,506,503 A | 4/1996 | Cecco | |
| 5,507,737 A | 4/1996 | Palmskog | |
| 5,713,939 A * | 2/1998 | Nedungadi et al. ............. 607/33 |
| 5,715,837 A | 2/1998 | Chen | |
| 5,733,313 A | 3/1998 | Barreras, Sr. et al. | |
| 5,948,006 A | 9/1999 | Mann | |
| 5,974,873 A | 11/1999 | Nelson | |
| 5,984,854 A | 11/1999 | Ishikawa | |
| 5,991,665 A | 11/1999 | Wang et al. | |

(Continued)

FOREIGN PATENT DOCUMENTS

| WO | WO00/66221 | 11/2000 |
|---|---|---|
| WO | WO03/039652 | 5/2003 |

OTHER PUBLICATIONS

International Search Report for PCT/US06/045458.

*Primary Examiner* — Deborah Malamud
(74) *Attorney, Agent, or Firm* — Beth L. McMahon; Medtronic, Inc.

(57) ABSTRACT

Techniques are disclosed for recharging an Implantable Medical Device (IMD). In one embodiment, a first external coil is positioned on one side of a patient's body, such as on a front side of the torso in proximity to the IMD. A second external coil is positioned on an opposite side of the patient's body, such as on the back of the torso. A recharging device generates a current in each of the coils, inductively coupling the first and the second coils to the secondary recharge coil of the IMD. According to another aspect, each of the two external coils may wrap around a portion of the patient's body, such as the torso or head, and are positioned such that the IMD lies between the coils. According to this aspect, current generated in the coils inductively couples to a second recharge coil that is angled within the patient's body.

11 Claims, 27 Drawing Sheets

(56) References Cited

U.S. PATENT DOCUMENTS

| | | |
|---|---|---|
| 6,009,350 A | 12/1999 | Renken |
| 6,047,214 A | 4/2000 | Mueller et al. |
| 6,058,330 A | 5/2000 | Borza |
| 6,102,678 A | 8/2000 | Peclat |
| 6,115,634 A | 9/2000 | Donders et al. |
| 6,212,430 B1 | 4/2001 | Kung |
| 6,275,737 B1 | 8/2001 | Mann |
| 6,315,769 B1 | 11/2001 | Peer et al. |
| 6,327,504 B1 | 12/2001 | Dolgin et al. |
| 6,345,203 B1 | 2/2002 | Mueller et al. |
| 6,366,817 B1 | 4/2002 | Kung |
| 6,371,905 B1 | 4/2002 | March et al. |
| 6,400,991 B1 | 6/2002 | Kung |
| 6,430,444 B1 | 8/2002 | Borza |
| 6,463,329 B1 | 10/2002 | Goedeke |
| 6,482,177 B1 | 11/2002 | Leinders |
| 6,505,077 B1 | 1/2003 | Kast et al. |
| 6,542,350 B1 | 4/2003 | Rogers |
| 7,107,103 B2 | 9/2006 | Schulman et al. |
| 7,158,021 B2 | 1/2007 | Hammett |
| 7,225,032 B2 | 5/2007 | Schmeling et al. |
| 7,428,438 B2 | 9/2008 | Parramon et al. |
| 7,471,986 B2 | 12/2008 | Hatlestad |
| 7,570,994 B2 | 8/2009 | Tamura et al. |
| 2003/0171792 A1 | 9/2003 | Zarinetchi et al. |
| 2004/0098068 A1 | 5/2004 | Carbunaru |
| 2004/0210254 A1 | 10/2004 | Burnett et al. |
| 2005/0075697 A1 | 4/2005 | Olson et al. |
| 2005/0137644 A1 | 6/2005 | Boveja |
| 2005/0228259 A1 | 10/2005 | Glukhovsky |
| 2007/0129767 A1 | 6/2007 | Wahlstrand |
| 2007/0255223 A1 | 11/2007 | Phillips |
| 2007/0276440 A1 | 11/2007 | Jacobson et al. |
| 2008/0027513 A1 | 1/2008 | Carbunaru |
| 2008/0300660 A1 | 12/2008 | John |

\* cited by examiner

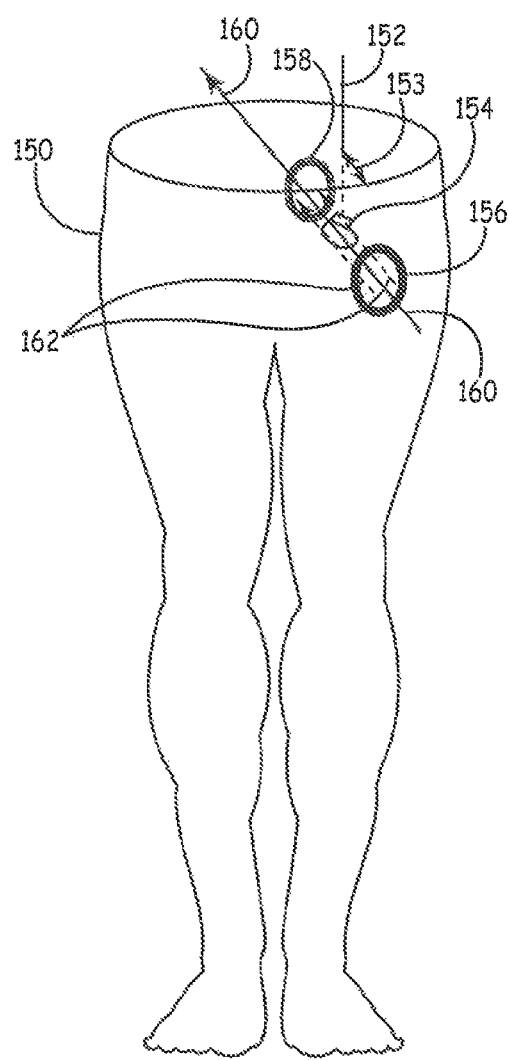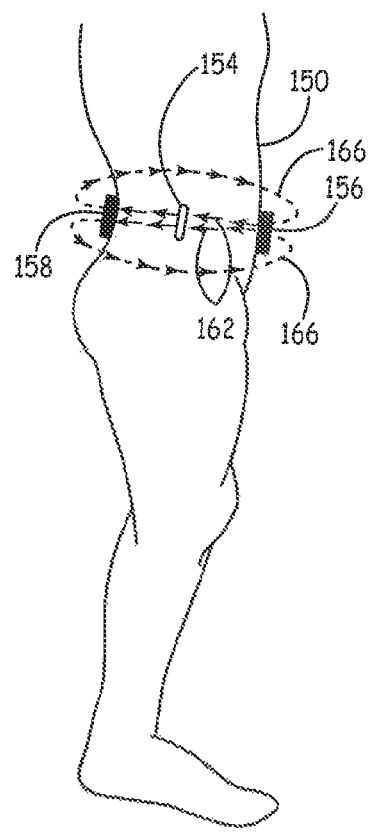
FIG. 4A
FIG. 4B

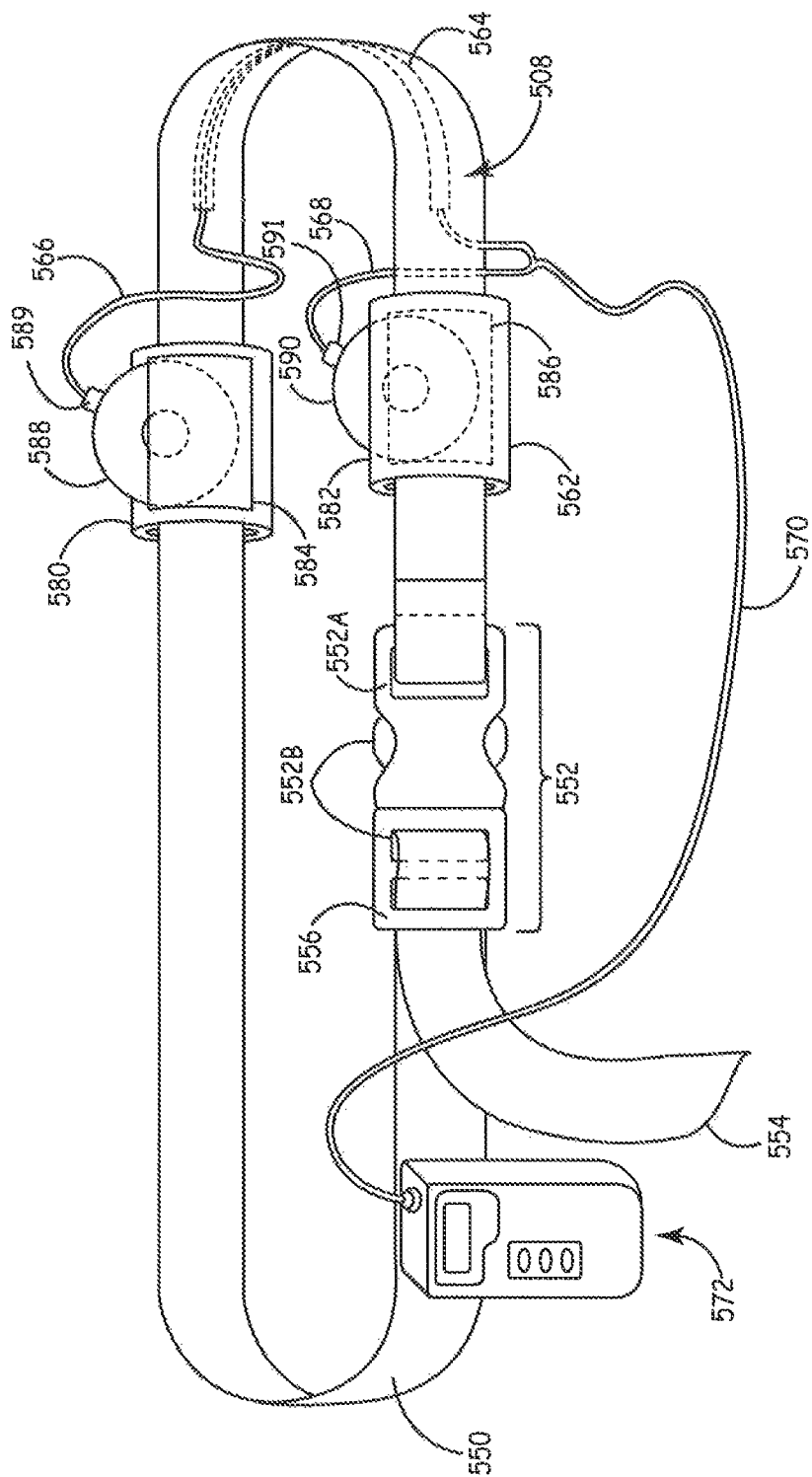

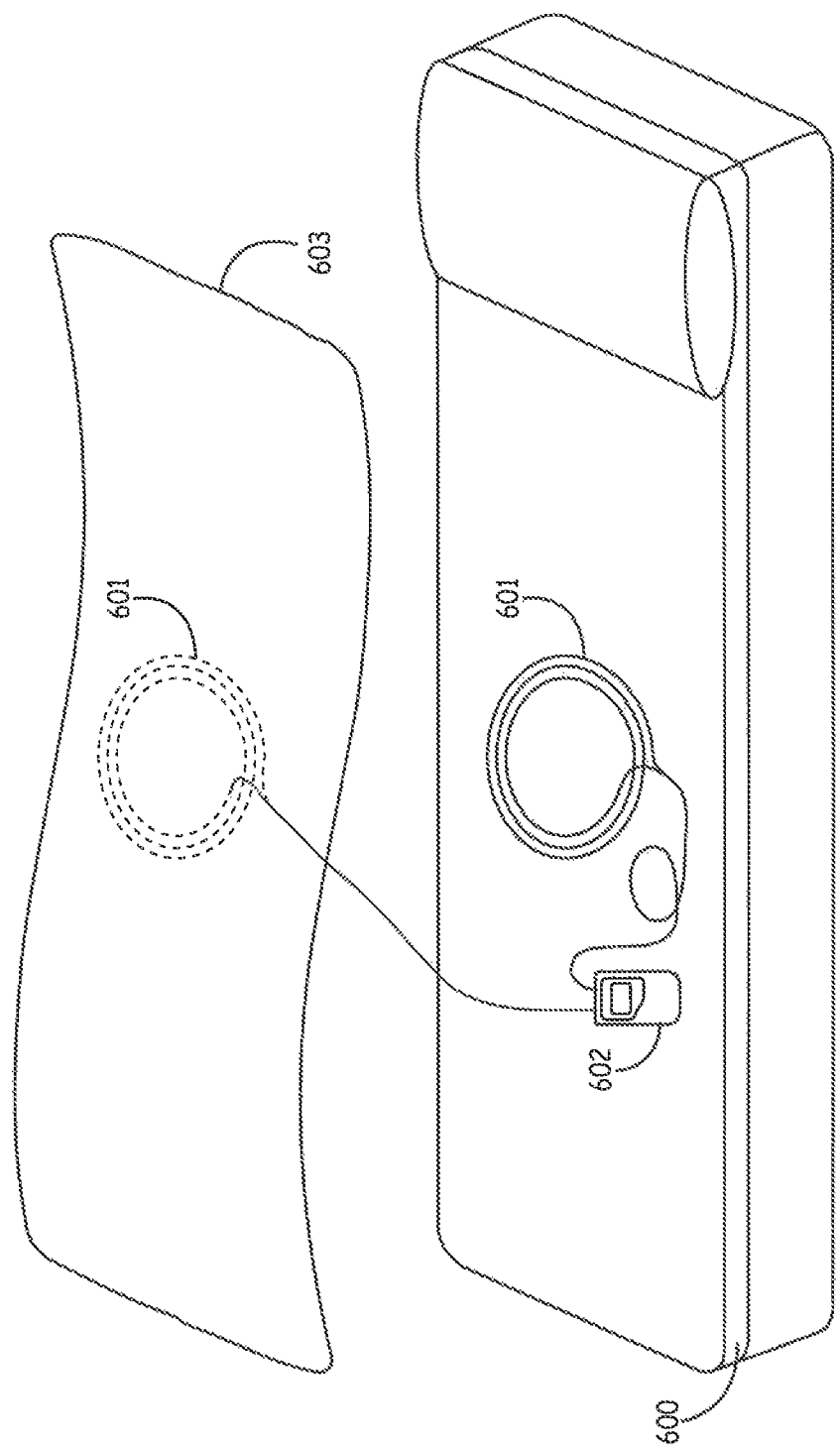

RECHARGE SYSTEM AND METHOD FOR DEEP OR ANGLED DEVICES

RELATED APPLICATIONS

This application is a continuation of, and claims priority to, U.S. patent application Ser. No. 12/108,051 filed Apr. 23, 2008, which issued as U.S. Pat. No. 8,204,602, which is incorporated herein by reference in its entirety.

FIELD OF THE INVENTION

This invention relates to IMDs and, in particular, to energy transfer devices, systems and methods for IMDs.

BACKGROUND OF THE INVENTION

Implantable Medical Devices (IMDs) for producing a therapeutic result in a patient are well known. Examples of such IMDs include, but are not limited to, implantable drug infusion pumps, implantable neurostimulators, implantable cardioverters, implantable cardiac pacemakers, implantable defibrillators and cochlear implants. Such IMDs may treat a variety of symptoms or conditions including, but not limited to, chronic pain, migraine headaches, tremor, Parkinson's disease, epilepsy, incontinence, gastroparesis, heart failure, tachycardia, and bradycardia.

A common element in all of these IMDs is the need for electrical power in the device. The IMD requires electrical power to perform its therapeutic function, which may include driving an electrical infusion pump, providing an electrical neurostimulation pulse and/or providing an electrical cardiac stimulation pulse, for example.

Typically, a power source for an IMD can take one of two forms. The first form utilizes an external power source that transcutaneously delivers energy via wires or radio frequency energy. Having electrical wires which perforate the skin is disadvantageous due, in part, to the risk of infection. Further, continuously coupling patients to an external power source for therapy is a large inconvenience.

A second type of power source utilizes single cell batteries as the energy source of the IMD. This can be effective for low-power applications, such as pacing devices. However, such single cell batteries usually do not supply the lasting power required to perform new therapies in newer IMDs. In some cases, such as an implantable artificial heart, a single cell battery might last the patient only a few hours. In other, less extreme cases, a single cell unit might expel all, or nearly all, of its energy in less than a year. This is not desirable due to the need to explant and re-implant the IMD or a portion of the device.

One way to address the aforementioned limitations involves transcutaneously transferring electrical power through the use of inductive coupling. Such electrical power may then be optionally stored in a rechargeable battery. In this form, an internal power source, such as a battery, can be used for direct electrical power to the IMD. When the battery has expended, or nearly expended, its capacity, the battery may be recharged. This is accomplished transcutaneously using electromagnetic coupling from an external power source that is temporarily positioned on the surface of the skin. Most often this will involve inductive coupling, but could include other types of electromagnetic coupling such as RF coupling.

Transcutaneous energy transfer through the use of electromagnetic coupling generally involves the placement of two coils positioned in close proximity to each other on opposite sides of the cutaneous boundary. An internal, or "secondary", coil is part of, or otherwise electrically associated with, the IMD. An external, or "primary", coil is associated with the external power source, or recharging device. The recharging device drives the primary coil with an alternating current. This induces a current in the secondary coil through inductive coupling. This current can then be used to power the IMD and/or to charge, or recharge, an internal power source.

For IMDs, the efficiency at which energy is transcutaneously transferred is crucial for several reasons. First, the inductive coupling has a tendency to heat surrounding components and tissue. The amount of heating of surrounding tissue, if excessive, can be deleterious. By increasing the efficiency of the energy transfer between the primary and secondary coils, heating of the tissue is minimized. Moreover, the time required to complete the recharge session is minimized, thereby maximizing patient convenience. Finally, if more energy may be transferred in a shorter period of time, IMDs may be employed that have higher power requirements and that provide greater therapeutic advantage to the patient.

One way to increase energy efficiency is to position the primary coil optimally with respect to the secondary coil. This generally involves positioning the primary coil on the patient's body (e.g., on their skin) as close to the secondary coil as possible. Moreover, the primary coil optimally lies in a plane that is parallel to the plane occupied by the secondary coil within the patient's body. This configuration is readily achieved in an implant scenario wherein the coil is implanted at a depth of between 1 and 3 centimeters in an orientation such that the IMD is positioned roughly parallel to the cutaneous boundary. This type of scenario may be used when an IMD is positioned within the pectoral region, as will be the case if the device is to be used to deliver electrical stimulation to areas of the brain, for instance.

In some cases, an IMD may be implanted more deeply within a patient's body. For instance, when an IMD is used to deliver therapy related to sacral nerve stimulation (SNS) as may be performed to treat incontinence, the IMD may be implanted more deeply within the abdominal cavity. When so implanted, the IMD may not be parallel to any particular cutaneous boundary, and in fact, may actually be perpendicular to such boundaries. As a result, less efficient recharge coupling is achieved, requiring longer recharge sessions.

SUMMARY OF THE INVENTION

In general, the invention is directed to techniques for recharging an IMD that is implanted more deeply within a patient's body (e.g., more than 3 cm) and/or that is angled within the body such that a secondary recharge coil of the IMD is not parallel to an adjacent body surface. In one embodiment, the invention relates to positioning a first external, or primary, coil ("first coil") on one side of a patient's body, such as on a front side of the torso proximal to the IMD. A second external coil ("second coil") is positioned on an opposite side of the patient's torso, such as on the back of the patient proximal to the IMD. A recharging device generates a current in each of the coils, electromagnetically coupling the first and the second coils to the secondary recharge coil of the IMD. The use of the two coils increases the electromagnetic coupling that is achieved for deep-implant scenarios, increasing efficiency with which a rechargeable power source may be recharged.

The above example describes first and second coils positioned on opposite sides of the torso. The mechanism is of particular use for an implant located within the torso, since IMDs located within this region may most likely be more than 3 cm from a cutaneous boundary. However, the mechanisms described herein may likewise be applied to an IMD located anywhere within a patient's body, including head, neck, arm, leg, chest, pectoral region, hand, foot, and so on.

As discussed above, one variation of the invention arranges two coils such that a surface of each coil is substantially flat against a surface of the patient's body. For instance, a first coil may be substantially flat against a front of the patient's torso while a surface of the second coil is substantially flat against the back of the patient's torso. This configuration is particularly effective in recharging an IMD that has a secondary recharge coil located in a plane that is substantially parallel to the front and back surfaces of the patient's body. In other words, this configuration is most effective if the IMD is not angled with respect to an adjacent surface of the patient's body. This is true because in this configuration, planes in which the first and second coils lie are substantially parallel to the plane carrying the secondary recharge coil of the IMD, which provides a scenario in which optimal coupling may be achieved between the first and second coils and the secondary recharge coil.

In another scenario, the IMD may be angled so that a plane carrying the secondary recharge coil is not substantially parallel to adjacent surfaces of the body. In a most extreme case, the secondary recharge coil may be carried in a plane that is transverse to the adjacent surfaces of the body. To address this type of scenario, an embodiment of the invention provides first and second coils that encircle, or are wrapped around, a portion of the body. The coils are positioned so that the IMD is located between the two coils. This provides a configuration in which planes carrying the first and second coils are substantially perpendicular to adjacent surfaces of the body and are substantially parallel to a plane carrying the secondary recharge coil. As discussed previously, this allows for better electromagnetic coupling between the first and second coils and the secondary recharge coil, thereby providing more efficient recharge of the rechargeable power source.

The first and second coils may be coupled to the recharging device in various ways within the scope of the invention. For instance, the first and the second coils may be electrically coupled in series to the recharging device such that the recharging device generates a current in both coils at once via a single port, or connection. Alternatively, each of the first and second coils may be connected to the recharging device via different ports, with the recharging device generating current in each of the coils independently. According to one aspect, each of the coils carries a current having the same amplitude, frequency, and phase.

Another aspect of the invention aligns the first and second coils according to a central major axis ("major axis"). As used herein, the major axis of the coil is the axis that intersects the center of the coil and is perpendicular to a plane in which the coil lies. The first and second coils may be aligned so that they substantially share the same major axis. According to another aspect, this major axis intersects the IMD, which lies between a first plane carrying the first coil and a second plane carrying the second coil.

A support structure or support member may be provided to support at least one of the first and second coils. This support structure may be a torso strap, a shoulder strap, or a holster. This support structure may allow at least one of the first and second coils to be selectably positioned. In one instance, the positioning is allowed to occur in two dimensions, such as vertically and horizontally relative to the patient's body. For instance, a holster may be provided that includes a first holder to receive or support the first coil and a second holder to receive or support the second coil. The first holder may generally be adjacent to the front of the patient's torso, and the second holder may be generally adjacent to the back of the patient's torso. Adjusters are provided to allow at least one, and optimally both, of the positions of the first and second holders to be adjusted in at least one of a vertical direction and a horizontal direction. In this manner, the first and second coils may be aligned relative to each other. For instance, the first and second coils may be aligned to have a same major axis.

In one embodiment, the support structure may be other than a holster, shoulder strap, or torso strap. For instance, it may be a garment such as a shirt, vest, shorts, sweat pants, or any other article of clothing that carries or supports the coils. In each case, the coils are positioned such that when the garment is donned, the coils are, in one embodiment, located on opposite sides of the patient's body. In another embodiment, when the garment is donned the coils encircle, or wrap around, a portion of the patient's body.

In the alternative, a support member may include headwear, such as a hat or a headset mechanism similar to that used to listen to a portable audio device. The headwear may position the coils on opposite sides of a patient's head, or may instead support the coils so that they each wrap around the head. As yet another example, the support member may include a neck support that carries coils on either side of an inner surface adapted to receive a patient's neck. Arm bands, leg bands, and head bands could likewise carry the coils. These coils could be adapted to position the coils on opposite sides of a portion of the patient's body, or instead to position the coils so they wrap around a portion of the patient's body.

Another embodiment of the invention provides two structures that carry or support the first and second coils, respectively. For instance, the first structure, which carries the first coil, may be a mechanism on which the patient sits, such as a chair or chair pad. A second structure, which carries the second coil, may be a torso strap, a garment, or some other structure that supports the second coil in a position that encircles the patient's body. The patient sits on the first structure while the second structure supports the second coil such that the IMD is located between the first and second coils.

According to another aspect, a first structure on which a patient lies is provided to carry the first coil. For example, this may include a mattress pad. A second item such as a blanket or other mechanism meant to cover the patient is provided to carry the second coil. The coils may be positioned on opposite sides of the body to recharge an IMD while the patient is resting.

One embodiment of the invention relates to a recharging system for use in recharging an IMD implanted in a patient. The IMD has a secondary recharge coil and a rechargeable power source. This recharging system includes a first coil lying in a first plane and a second coil lying in a second plane substantially parallel to the first plane. The IMD lies between the first and second planes. A recharging device is coupled to each of the first and the second coils to generate a current in the first and the second coils that electromagnetically couples the first and the second coils to the secondary recharge coil to recharge the rechargeable power source.

In the foregoing embodiment, the first coil is said to lie in a first plane and the second coil is said to lie in the second plane. It should be noted that this does not necessarily mean that all turns of a multi-turn coil lie within a same plane. For instance, multiple turns of a first coil may be stacked one on top of another such that the turns reside in different planes. In this case, the coil may be said to be carried, or lie within, multiple planes. Each of these multiple planes will be substantially parallel to one another, and substantially perpendicular to a major axis of the coil. Thus, a first plane carrying a first coil may be any one of multiple planes in which the first coil lies. Likewise, a second plane carrying the second coil may be one of multiple planes in which the second coil lies.

Another aspect of the invention relates to a recharging system for use in recharging an IMD implanted in a patient. The IMD has a secondary recharge coil and a rechargeable power source. The recharging system comprises first and second coils external to the patient's body and positioned so that the IMD lies between the first and second coils with a major axis of at least one of the first and second coils intersecting the IMD. A recharging device is coupled to generate a current that electromagnetically couples the first and the second coils to the secondary recharge coil to recharge the rechargeable power source.

Another aspect relates to a method of recharging a rechargeable power source of an IMD implanted within a patient. The method includes providing a first coil and a second coil that lie in a first plane and a second plane, respectively. The first and second coils are external to the patient's body. The coils are positioned such that the IMD lies between the first and the second planes and the first and the second planes are substantially parallel to each other. A current is generated in the first coil and the second coil to electromagnetically couple the first and the second coils to a secondary coil of the IMD to recharge the rechargeable power source.

Other aspects of the invention will become apparent to those skilled in the art from the following description and the accompanying Figures.

BRIEF DESCRIPTION OF THE DRAWINGS

FIG. 4A is a front perspective view of a lower portion of human torso in which an Implantable Medical Device is implanted.

FIG. 4B is a side view of human torso that corresponds to the configuration shown in FIG. 4A.

FIG. 12B is a perspective view of an alternative embodiment of the torso strap shown in FIG. 12A.

FIG. 13F is a side perspective view of an embodiment that carries a first coil on a support structure on which the patient lies and an accompanying item carrying a second coil that is adapted to cover the patient as the patient is in the prone position.

DETAILED DESCRIPTION OF THE INVENTION

Figure 1:
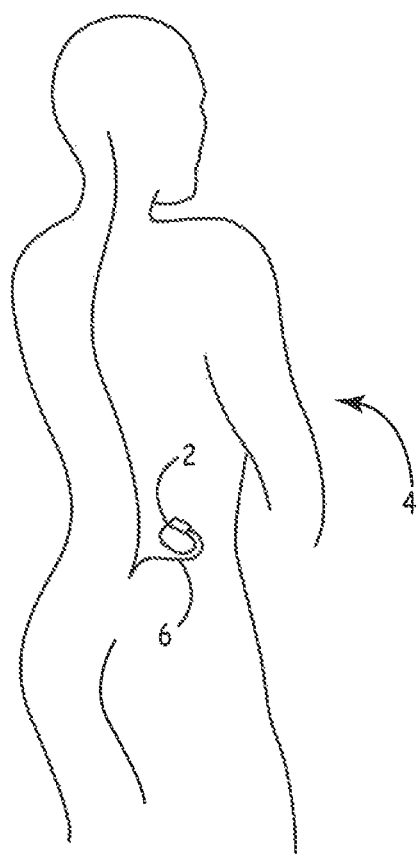
FIG. 1 is a diagram of an Implantable Medical Device implanted in a patient.

FIG. 1 shows an exemplary IMD 2, which may be a neurostimulator, implanted in patient 4. For instance, the IMD may be implanted within the abdominal cavity at a depth of greater than 3 centimeters from the patient's skin, which is considered a "deep-implant scenario". Furthermore, IMD 2 may be angled such that a secondary recharge coil contained within, or otherwise associated with, the IMD is not parallel to a surface, or "cutaneous boundary", of the patient's body. Moreover, at a given point in time, the exact angle of the secondary recharge coil relative to a cutaneous boundary may be difficult to determine. This is so because that angle may change slightly over time based on a patient's posture and/or the surgical approach that was used during implant.

IMD 2 can be any number of medical devices such as an implantable therapeutic substance delivery device, an implantable drug pump, a cardiac pacemaker, a cardioverter or defibrillator, a device to deliver electrical stimulation pulses for a neurological or muscular condition, a device to deliver electrical stimulation to alleviate pain, or any other IMD for delivering therapy. This therapy may be delivered via one or more therapy connections 6, which may be one or more leads and/or catheters.

Figure 2:
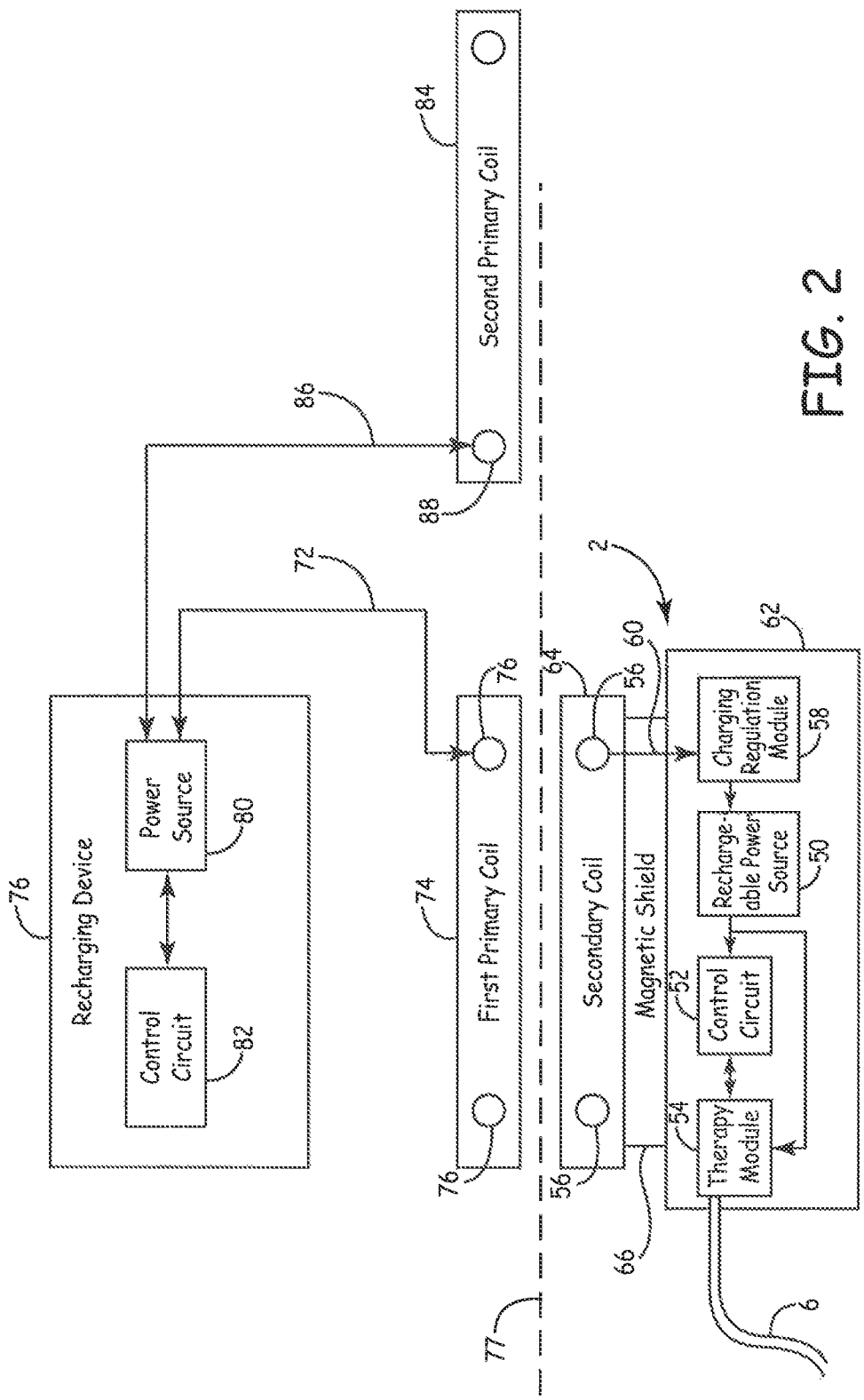
FIG. 2 is a more detailed block diagram of an Implantable Medical Device situated under a cutaneous boundary with a recharging device positioned proximate to the cutaneous boundary.

FIG. 2 is a block diagram of one embodiment of IMD 2. According to the current invention, IMD 2 includes a rechargeable power source 50. Rechargeable power source 50 can be any of a variety of rechargeable power sources including a chemically-based battery or a capacitor. In one embodiment, rechargeable power source 50 is a lithium ion battery. Any other type of rechargeable battery suitable for powering an IMD may be used according to the current invention.

Rechargeable power source 50 is coupled to a control module 52, which includes circuitry to control therapy delivered to the patient. Control module 52 may include one or more microprocessors, application-specific integrated circuits (ASICs), digital signal processors (DSPs), field-programmable gate arrays (FPGAs), discrete electronic components, state machines, sensors, and/or other circuitry.

Control module 52 is further coupled, and provides power, to therapy module 54. Therapy module 54 delivers some form of therapy to a patient. This therapy may include controlled delivery of a substance and/or electrical stimulation. For example, in one embodiment, therapy module 54 may include one or more output pulse generators such as capacitive elements, voltage regulators, current sources, and/or switches that are coupled to rechargeable power source 50 directly or through control circuit 52. Therapy module 54 may deliver electrical pulses to patient 4 via a combination of electrodes. Therapy module 54 is coupled to patient 2 through one or more therapy connections 6 such as leads and/or catheters.

In one embodiment, rechargeable power source 50 is coupled to a secondary coil 56 (shown in cross-section) through a charging regulation module 58. During a recharge session, a current is induced in secondary coil 56 in a manner to be discussed below. This current is provided via connection 60 to charging regulation module 58, which controls the charging of rechargeable power source 50.

Rechargeable power source 50, charging regulation module 58, control circuit 52, and therapy module 54 are generally contained in a hermetically sealed housing 62. Secondary coil 56 may be attached to, or positioned on, an exterior surface of sealed housing 62 through connection 60. For instance, secondary coil 56 may be contained within a second housing 64 that is positioned adjacent to sealed housing 62. In an alternative embodiment, secondary coil 56 may be contained in housing 62 along with the other electronics.

In one embodiment, a magnetic shield 66 may be positioned between secondary coil 56 and housing 62. The primary purpose of magnetic shield 66 is to substantially increase the amount of energy captured by the secondary coil. Magnetic shield 66 also protects rechargeable power source 50, control circuit 52, therapy module 54 and charging regulation module 58 from electromagnetic energy when secondary coil 56 is utilized to charge rechargeable power source 50.

FIG. 2 further illustrates an external recharging device 70 which may be used to recharge rechargeable power source 50. External charging device 70 is coupled via cable 72 to an antenna 74 (shown in cross-section). In an alternative embodiment, charging device 70 and antenna 74 may be combined into a single unit.

Antenna 74 includes a first primary coil 76 ("first coil", shown in cross-section). During a recharge session, primary coil 76 is positioned proximate to secondary coil 56 on an opposite side of cutaneous boundary 77 (shown dashed). Charging device 70 generates a current in first primary coil 76. When first primary coil 76 is positioned proximate to secondary coil 56, the current in primary coil 76 electromagnetically couples this primary coil to secondary coil 56. In the current embodiment, this electromagnetic coupling is inductive coupling, although other forms of coupling (e.g., RF coupling) are possible. The electromagnetic coupling results in a current being generated in secondary coil 56. This current is provided to charging regulation module 58, which controls a rate at which rechargeable power source 50 is recharged.

Recharging device 70 drives primary recharge coil 76 via power source 80. Power source 80 may be rechargeable. For instance, power source 80 may include rechargeable batteries to allow a patient who is engaged in a recharge session to be somewhat ambulatory during this process. In this embodiment, a desktop charging device (not shown) which is coupled to an AC or DC power source (e.g., via a wall outlet) may be used to periodically recharge power source 80 when recharging device 70 is not in use. In another embodiment, recharging device 70 may be coupled directly to a source of AC power, such as a standard wall outlet during the recharge session.

Recharging device 70 may further include a control circuit 82. Control circuit 82 initiates and controls recharging sessions with IMD 2. Control circuit 82 may include one or more microprocessors, FPGAs, ASICs, DSPs, microsequencers, discrete components, and/or other electronic circuit components.

According to one embodiment of the current invention, recharging device 70 may be coupled to a second antenna 84 via cable 86. Antenna 84, like antenna 74, includes a second primary coil 88 ("second coil", shown in cross-section). Power source 80 is capable of driving both of primary coils 76 and 88 at the same time so that a current is produced in each of the coils having the same amplitude, frequency, and phase. First and second primary coils 76 and 88, respectively, may be positioned in a manner that generates a higher flux density through secondary coil 56 than would be created using only one of primary coils 76 or 88. As a result, a more efficient recharge of rechargeable power source 50 may be achieved. This is discussed further below.

It will be appreciated that recharging device 70 and IMD 2 are merely exemplary. Many alternative configurations are possible for both of these devices. For instance, both recharging device 70 and IMD 2 may include telemetry coils and control circuits for supporting telemetry communication between the two devices. Moreover, the various logical functions may be partitioned differently. For instance, the control circuit 52 and therapy module 54 of IMD 2 may be combined into a single logic block, and so on. Thus, the implementations shown in FIG. 2 are to be considered illustrative in nature only.

In FIG. 2, secondary coil 56 is shown proximate to cutaneous boundary 77, with the plane in which this coil lies being approximately parallel to cutaneous boundary 77. This allows a magnetic field generated by a current within first primary coil 76 to readily couple with secondary coil 56. Efficient inductive coupling may be harder to achieve when secondary coil 56 is farther away from cutaneous boundary 77 (e.g., more than 3 centimeters away) and/or if the plane in which secondary coil 56 lies is not parallel to cutaneous boundary 77. This results in less efficiency energy transfer between first primary coil 76 and secondary coil 56.

Figure 3:
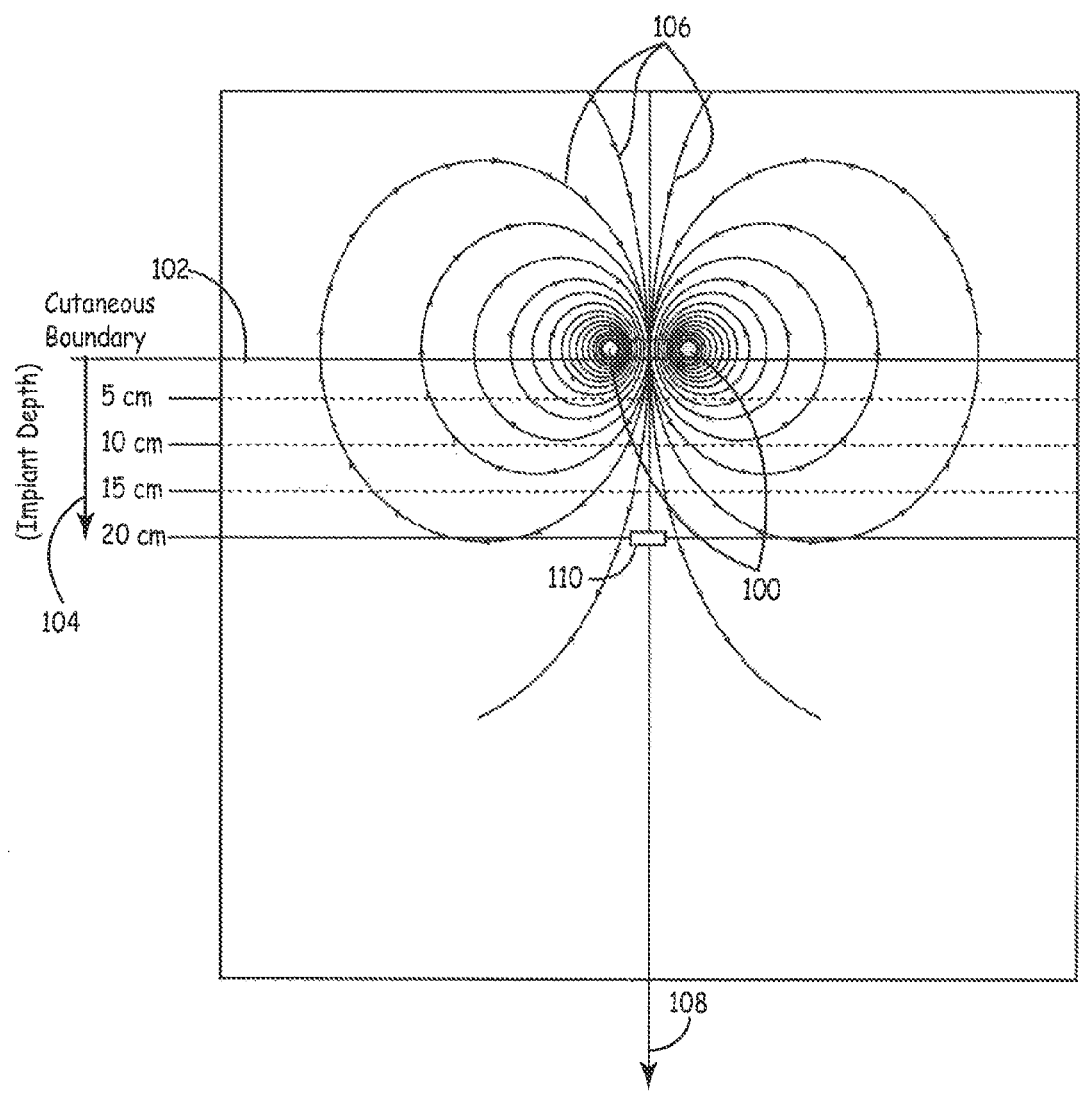
FIG. 3 is a flux diagram illustrating that the flux density decreases as implant depth increases.

FIG. 3 is a flux diagram illustrating the magnetic flux lines produced by a 100-turn flat (i.e., "pancake") coil 100 that is ten centimeters in diameter. This type of coil may be constructed of conductive wire formed of copper or some other conductive material, which may be stranded. It will be assumed coil 100 carries a current of 1 milliamp (mA). For purposes of this example, it will be assumed that coil 100, which is shown in cross-section, corresponds to first primary coil 76 of recharging device 70.

Coil 100 has a central major axis 108. A central major axis ("major axis") refers to an axis that intersects the center of the coil and is perpendicular to the plane in which the coil lies.

In FIG. 3, X-axis 102 represents a cutaneous boundary. Coil 100 is positioned in close proximity to, and substantially parallel with, this boundary, as would occur when the coil is positioned on a patient's skin in preparation to initiate a recharge session. Implant depth is represented by Y-axis 104, and increases as one moves away from cutaneous boundary 102.

FIG. 3 further includes flux lines (e.g., flux lines 106). As known in the art, these flux lines indicate the relative strength and direction of the magnetic field at any given location relative to coil 100. In particular, the density of the flux lines (that is, the "flux density") is proportional to the magnitude of the local magnetic field vector. As may be seen in FIG. 3, the flux density is highest close to the coil. For instance, at a point along axis 108 that is close to cutaneous boundary 102, such as that corresponding to an implant depth of 3 cm or less, the flux lines are relatively close together. At a distance of 3 cm, for instance, the flux density is roughly 2000 nT. As such, if a secondary coil were positioned substantially at this location, as would occur if an IMD were implanted relatively close to the skin, efficient inductive coupling would be achieved between coil 100 and this secondary coil.

FIG. 3 further illustrates that the flux density decreases dramatically as implant depth increases. For instance, assume an IMD is positioned along axis 108 at an implant depth of 20 centimeters, and lies within a plane roughly parallel to a plane carrying coil 100. This is represented by location 110. In this scenario, the flux density at the implant location 110 has been reduced to 180 nanoTeslas (nT), which is not adequate to support an efficient recharge session. Thus, a single "pancake" coil is not effective for recharging an IMD used in the type of deep implant situation represented by FIG. 3.

The current invention provides several coil configurations that increase flux density to improve recharge coupling efficiency for deep-implant scenarios, and situations wherein the secondary recharge coil of an IMD is not necessarily positioned in a plane parallel to the cutaneous boundary.

FIG. 4A is a front perspective view of a lower portion of human torso 150. Assume an IMD 154 has been implanted within a patient represented by torso 150 at a deep-implant location that is more than 3 cm from any adjacent cutaneous boundary of torso 150. That is, the distance represented by arrow 153 between an adjacent cutaneous boundary and the implant location represented by line 152 is more than 3 cm.

A first coil 156 is positioned on a first side of torso 150, which in this example is the front of torso. A second coil 158 (shown dashed) is positioned on an opposing, or opposite, side of torso from the first side. In this example, secondary coil 158 is positioned on a back side of torso 150. Coils 156 and 158 are positioned so that the two planes in which the coils lie are substantially parallel to each other. Moreover, these coils may also be substantially parallel to a third plane in which IMD 154 lies. Additionally, these coils may be roughly positioned so that both coils share a major axis 160. As discussed previously, a major axis of a coil is an axis that substantially intersects the center of the coil and which is perpendicular to the plane in which the coil lies. In one specific embodiment, the coils may be positioned so that major axis 160 intersects IMD 154. According to one aspect, major axis 160 may substantially coincide with a major axis of a secondary coil of IMD 154.

Currents induced in the clockwise direction of both coils 156 and 158 result in magnetic flux lines 162 that are roughly perpendicular to the plane in which IMD 154 lies. Moreover, the flux density at IMD 154 that is produced by the two coils 156 and 158 is much greater than that produced if only a single coil were employed. This is discussed in more detail in relation to FIG. 5.

FIG. 4B is a side view of human torso 150 that corresponds to the configuration shown in FIG. 4A. Coil 156 (shown in cross-section) is positioned proximate the front of torso 150, and coil 158 (also shown in cross-section) is positioned proximate the back of torso 150. When current is induced in both coils in a clockwise direction in the manner shown in FIG. 4A, magnetic flux is produced that flows through the middle of both coils from the front to the back of torso 150. These flux lines 162 flow through IMD 154 (shown in cross-section), and would inductively couple with a secondary coil lying in the plane of IMD 154. Returning flux lines 166 flow from secondary coil back to primary coil, completing the magnetic circuit. Using this configuration, the density of flux lines 162 coupling with the secondary coil of IMD is significantly greater than would be achieved if only a single coil were used.

Figure 5:
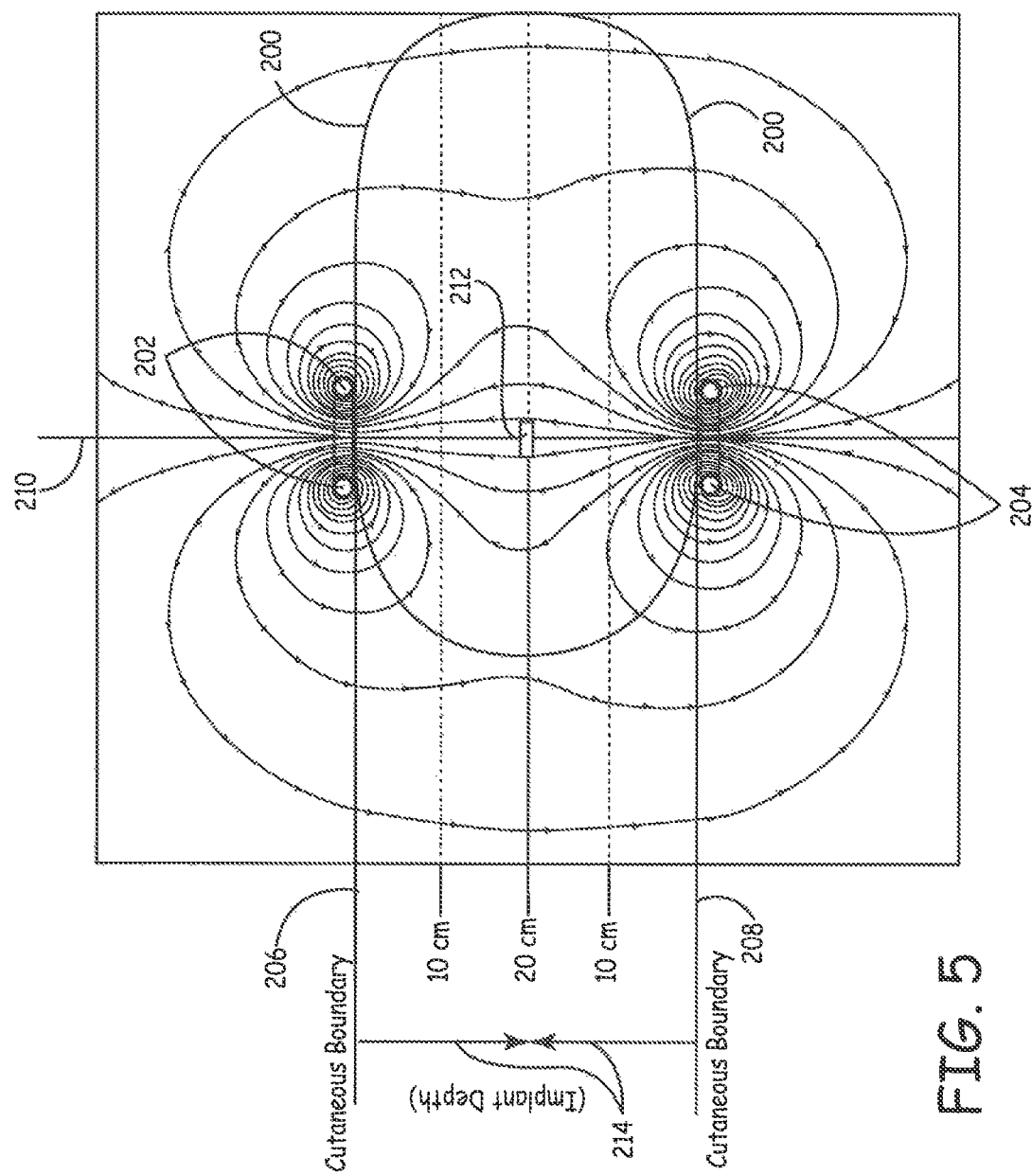
FIG. 5 is a flux diagram showing flux density relative to the torso of FIGS. 4A and 4B.

FIG. 5 is a flux diagram illustrating the magnetic flux lines produced by two coils that are each similar to the coil employed to produce the diagram of FIG. 3. That is, each of the coils is a 100-turn pancake coil that is ten centimeters in diameter and carries a current of 1 mA.

FIG. 5 represents flux flowing through a cross section of torso 150, the outline of which is indicated by outline 200. Coils 202 and 204 (shown in cross-section) are positioned at cutaneous boundaries 206 and 208, respectively, of torso outline 200. This represents the scenario wherein coils 202 and 204 are located on opposing sides of the torso, which in this example are the front and back of a torso, respectively. This corresponds to the positioning of coils 156 and 158 on torso 150 of FIGS. 4A and 4B. In another embodiment, it is possible to position the coils on opposing sides of torso, rather than the torso front and back.

Major axis 210 intersects the centers of both coils 202 and 204 and is substantially perpendicular to the planes that carry these coils. The distance between the centers of coils 202 and 204 along axis 210 is 40 cm, as indicated by arrows 214. A position 212 may be identified along line 210 that is equidistant from the centers of both coils. That is, position 212 is roughly 20 cm from the center of each of the coils, as shown by arrows 214. At this position, the flux density is roughly 305 nT. This is considerably greater than the flux density of 180 nT that would be achieved if either coil 202 or 204 were used alone. Thus, the use of dual pancake coils positioned on the front and back of the torso greatly increases the flux density at a deep implant position located along a line that intersects the centers of the coils, such as position 212 that is roughly equidistant from the center of both the coils.

Figure 6:
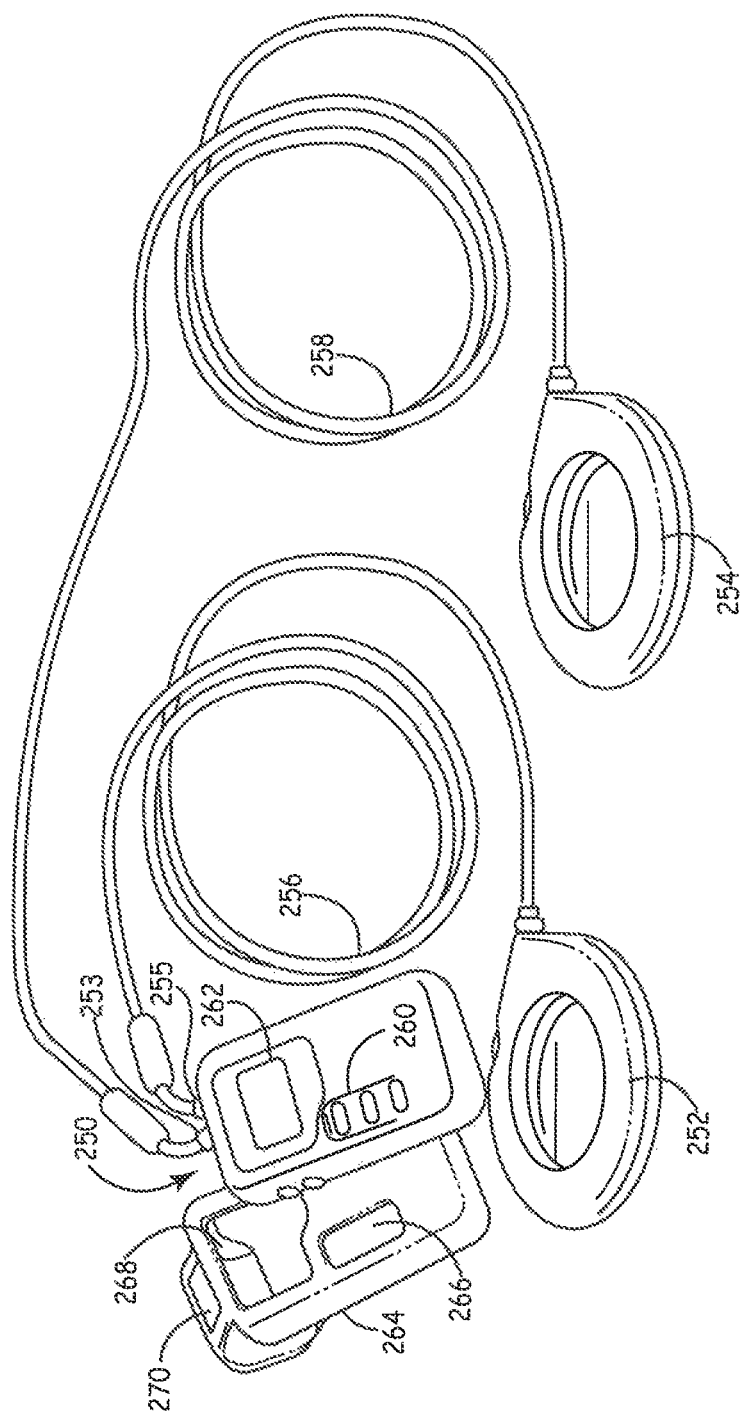
FIG. 6 is a front perspective view illustrating one embodiment of an external recharging device that may be used to recharge a rechargeable power source according to the current invention.

FIG. 6 is a front perspective view illustrating one embodiment of an external recharging device 250 that may be used to recharge a rechargeable power source according to the current invention. External recharging device 250 is coupled to first and second primary coils 252 and 254 via cables 256 and 258, respectively. Electronics within external recharging device 250 drive coils 252 and 254 via separate ports 253 and 255, respectively, to produce a current. In one embodiment, the current generated in coil 252 has the same frequency, phase and amplitude as that generated in coil 254. Coils 252 and 254 may be positioned on opposites sides (e.g., a front and a back, or a left and right side) of torso, respectively, in the manner shown in FIGS. 4A, 4B, and 5 to increase the flux density produced at a deep-implant location such as one that is approximately more than 3 cm from either coil.

Controls 260 are provided on the front of recharging device 250 to allow a patient or a clinician to initiate and control the recharging of an implanted IMD. In one embodiment, recharging device 250 supports a first mode wherein recharging device generates a current in a selected one of coils 252 and 254. This allows a single one of coils 252 or 254 to be used to recharge a rechargeable power source carried by an IMD located relatively close (e.g., roughly 3 cm or less) from a cutaneous boundary. A second mode is provided wherein recharging device 250 generates a current in both coils in the manner discussed above to recharge an IMD implanted more deeply within the body. Status regarding operation of recharging device 250 may be provided via display screen 262.

FIG. 6 further illustrates an optional recharger holder 264 that receives recharging device 250. Holder 264 may be fashioned to include a cutaway portion 266 that allows a patient to access controls 260. A second cutaway portion 268 may be provided to allow a patient to view display screen 262 of recharging device 250. A third cutaway portion 270 may be provided to allow cables 256 and 258 to couple to recharging device 250. During a recharge session, recharger holder 264 may be coupled to a strap, belt, or some other support member carried on, or worn by, the patient (not shown in FIG. 6). Alternatively, recharging device 250 may be carried in a pocket of the patient's clothing, or attached to a hook or some other support member carried on, or worn by, the patient without the use of recharger holder 264.

Figure 7A:
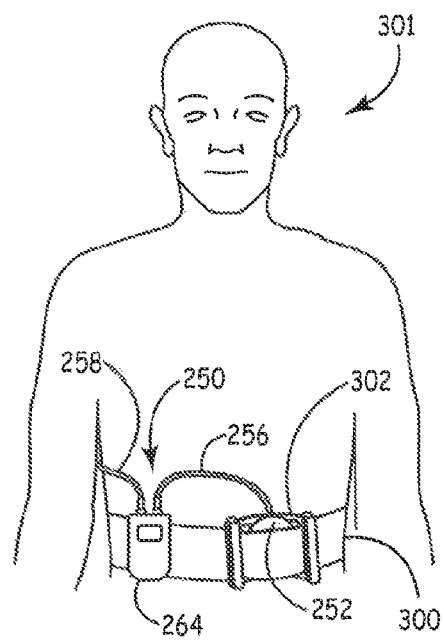
FIG. 7A is a front perspective view of a patient using a dual-coil recharging device of a type similar to that shown in FIG. 6.

FIG. 7A is a front perspective view of a patient 301 using a dual-coil recharging device of the type shown in FIG. 6. The patient has donned a torso strap 300 (e.g., a belt), which may be formed of any durable flexible material such as nylon, cotton, leather, and the like. Torso strap 300 may be retained around the patient's torso via any type of fastener, such as hook-and-eye strips (e.g., VELCRO® fasteners), buckles, snaps, belts, ties, buttons, and so on. Torso strap 300 engages or otherwise carries a first coil holder 302 ("first holder"). In one embodiment, first holder 302 slidably engages torso strap 300, as may be accomplished by threading torso strap 300 through slots included in sides of first holder 302. In this manner, first holder 302 may be slidably positioned along torso strap 300 to a selected location that is proximate to an implant location, as will be discussed below. When so positioned on the torso strap, first holder 302 forms a pocket that is sized to receive one of coils 252 or 254 of recharging device 250.

Torso strap 300 may also be coupled to recharger holder 264 (FIG. 6), as may be accomplished via a belt clip, hook, or some other support member(s). Recharger holder 264 carries recharging device 250, which is shown coupled to cables 256 and 258. Cable 256 is, in turn, coupled to coil 252 in the manner shown in FIG. 6. Coil 252 is inserted into the pocket formed between first holder 302 and torso strap 300.

Figure 7B:
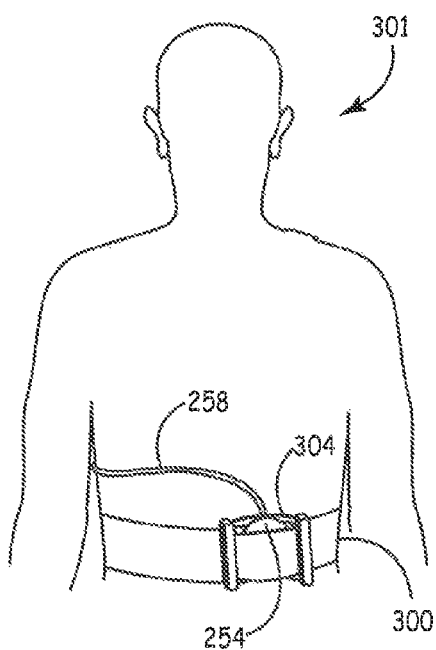
FIG. 7B is a back perspective view of patient of FIG. 7A employing the dual-coil recharging device.

FIG. 7B is a back perspective view of patient 301 of FIG. 7A. Torso strap 300 encircles the torso of the patient. Cable 258, which is coupled to recharging device 250 in the manner shown in FIG. 7A, encircles the patient's right side and is coupled to coil 254. Coil 254 is inserted within a second holder 304. Like first holder 302 of FIG. 7A, second holder 304 forms a pocket with torso strap 300 that is sized to receive coil 254. In one embodiment, second holder 304 includes slots along its side through which torso strap 300 is threaded. Second holder 304 may thereby be slidably positioned along belt to a selected location. By positioning first and second holders 302 and 304 along belt, they may be aligned substantially as shown in FIGS. 4A, 4B, and 5. That is, the major axis that intersects the centers of coils 302 and 304 also intersects an IMD implanted within patient 301. Recharging device 250 may then be used to generate a current within coil 252 that has the same frequency, amplitude, and phase as that generated within coil 254. This produces a flux density at the implant location in a manner similar to that shown in FIG. 5. This flux density is sufficient to support an efficient recharge session to recharge a rechargeable power source contained within the IMD, even when IMD is situated at a deep-implant location.

Figure 7C:
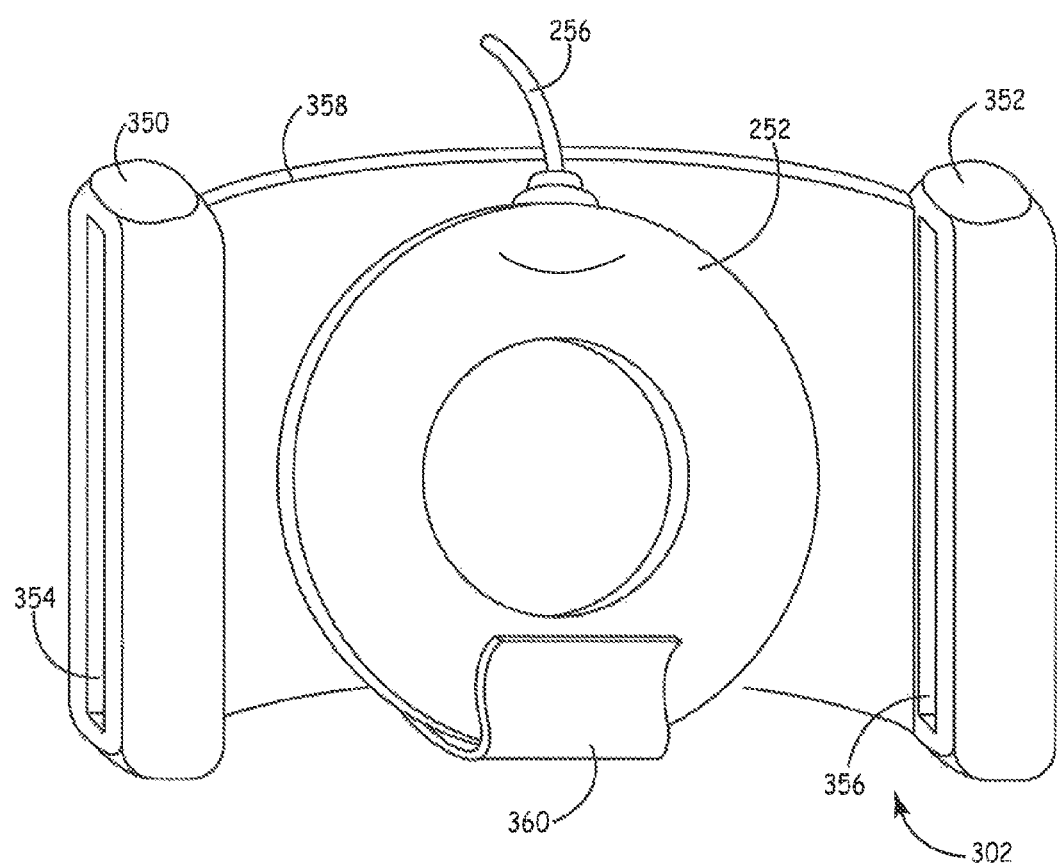
FIG. 7C is a front perspective view of one embodiment of a coil holder of FIG. 7A.

FIG. 7C is a front perspective view of one embodiment of first holder 302 of FIG. 7A. A similar configuration may be used for second holder 304 of FIG. 7B. Holder 302 includes side portions 350 and 352, which may be constructed of a durable material such as polyurethane. Side portions 350 and 352 include slots 354 and 356, respectively, to receive torso strap 300.

Each of side portions 350 and 352 are coupled to a flexible strap 358 which may be made of nylon, leather, cotton, or some other suitable material. Strap 358 may be coupled to a clip 360 or some other support member provided to support coil 252 in the manner shown. Alternatively, coil 252 may be held in position solely by threading torso strap 300 through slots 354 and 356 and tightening the belt such that belt and strap 358 exert pressure on coil 252.

Figure 7D:
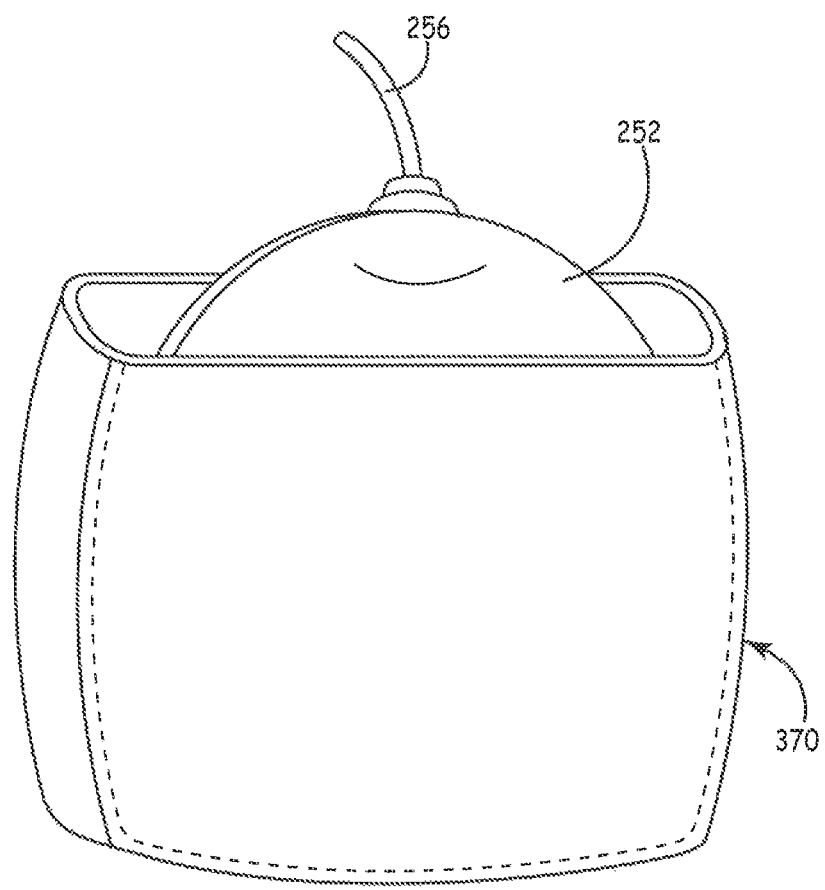
FIG. 7D is a front perspective view of another embodiment of a coil holder.

FIG. 7D is a front perspective view of another embodiment of a coil holder suitable for use as first and second holders 302 and 304 of FIGS. 7A and 7B. In this embodiment, the coil holder is a pouch 370 of a type that may be configured from a material such as nylon, cotton, leather, or any other durable fabric. Pouch 370 is sized to receive coil 252. Pouch includes a mechanism for connecting it to torso strap 300, such as via one or more clips, hooks, snaps, ties, buttons, hook-and-loop fastening strips, and/or any other support member(s). Alternatively, slots or belt loops may be provided in pouch 370 through which torso strap 300 may be threaded in a manner similar to that discussed in regards to FIG. 7C. Preferably, the connecting mechanism allows for selective positioning of the pouch along torso strap 300.

In yet another embodiment, some type of fastening member may be coupled directly to, or provided by, coils 252 and 254. For instance, each coil may be integrally formed with a belt clip or other fastener that is provided to couple the coils directly to the torso strap without use of an additional holder.

In FIGS. 7A-7D, coils 252 and 254 are shown carried in pockets associated with torso strap 300. In this type of embodiment, belt must be positioned at a height that corresponds substantially with the height of the implant within a patient's body. In some situations, this may be undesirable. For instance, implant may be positioned within the abdominal cavity in a location that is adjacent to a patient's rib cage. In this instance, it may not be comfortable to encircle torso strap 300 around the torso at the same height as the implant. In this case, coils 252 and 254 may be carried in pockets associated with a shoulder strap.

Figure 8A:
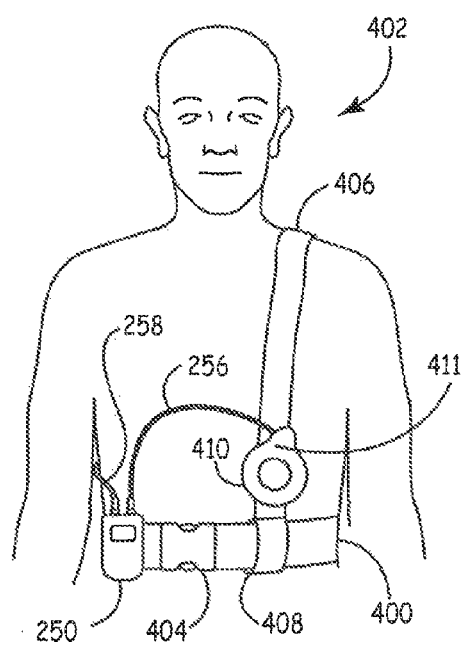
FIG. 8A is a front view of one embodiment of a holster that may be used to carry two coils according to the current invention.

FIG. 8A is a front view one embodiment of a holster that may be used to carry coils 252 and 254 according to the current invention. In this embodiment, a torso strap 400 encircles torso of patient 402. Torso strap 400 is maintained around the patient's torso by a fastener 404, which may be a clip, a buckle, hook-and-loop fasteners, or any other type of fastening device.

Torso strap 400 engages a shoulder strap 406. For example, an end of shoulder strap 406 may be configured to form a loop 408 that slidably engages torso strap 400. Shoulder strap 406 extends over a shoulder of patient 402 to the patient's back. Shoulder strap 406 carries a first coil holder 410 ("first holder") which may be a pocket formed of a durable, flexible material such as nylon, cotton, or leather, and is adapted to hold a respective one of coils 252 and 254 of recharging device 250 (FIG. 6). In FIG. 8A, first holder 410 is shown to hold coil 252, which is coupled to cable 256. In one embodiment, first holder 410 may have a tab 411 that can be readily grasped to pull open the pocket and insert one of coils 252 and 254. First holder 410 of one embodiment may be selectively positionable relative to shoulder strap 406. This is discussed further below. According to one aspect, first holder 410 may be configured in a manner described by commonly-assigned U.S. patent application entitled "Holster for Charging Pectorally-Implanted Medical Devices", U.S. patent application Ser. No. 12/061,055, filed Apr. 2, 2008.

Torso strap 400 may be further coupled to recharger holder 264, as may be accomplished via a belt clip, some other type of fastener, or via slots within the recharger holder through which torso strap may be threaded. Recharge holder 264 supports recharging device 250, which is coupled via cable 256 to coil 252, which is shown inserted within first holder 410. Recharging device 250 is further coupled to cable 258, which extends to second coil 254 (not shown in FIG. 8A).

Figure 8B:
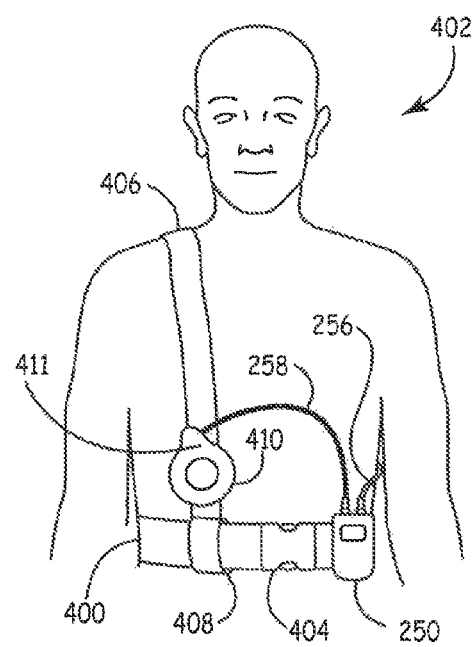
FIG. 8B is a front view of the embodiment of the holster of FIG. 8A with the shoulder strap over the patient's right shoulder.

FIG. 8B is a front view of the embodiment of the holster of FIG. 8A with shoulder strap 406 having been donned over the patient's right, rather than left, shoulder. In FIGS. 8A and 8B, like elements are designated with the same numeric identifiers. As was the case in FIG. 8A, loop 408 may be slid along torso strap 400 to further adjust the lateral (i.e., horizontal) position of coil holder 410.

Figure 9A:
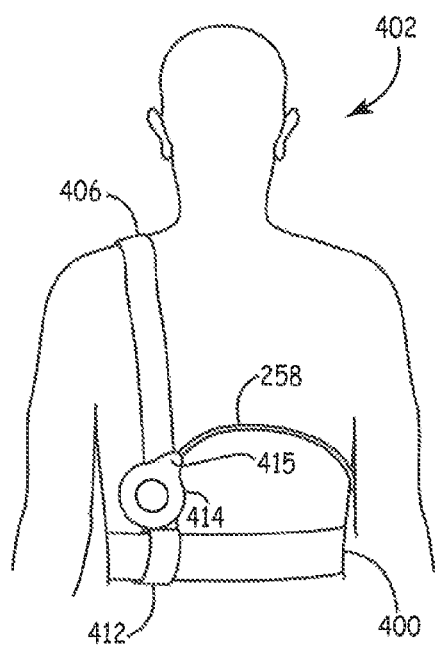
FIG. 9A is a back view of a patient donning the holster of FIGS. 8A and 8B.

FIG. 9A is a back view of patient 402 and the holster of FIGS. 8A and 8B. In particular, the holster has been donned over the patient's left shoulder in the manner shown in FIG. 8A and engages torso strap 400. In one embodiment, this is accomplished by providing a loop 412 at a back end of shoulder strap 406. Loop 412 receives, and slidably engages, torso strap 400. In other embodiments, shoulder strap 406 may engage torso strap 400 in a different manner such as with hooks, ties, hook-and-loop strips, or other fastening means.

Shoulder strap 406 carries a second coil holder 414 ("second holder") which is adapted to support or receive one of coils 252 and 254 of recharging device 250 (FIG. 6). Second holder 414 may be a pocket formed out of a durable flexible material such as nylon, cotton, or leather, for instance. Second holder 414 may have a tab 415 that may be grasped to spread the pocket of holder so that a coil may be readily inserted. For instance, the holder may be fashioned in a manner similar to that described in the commonly-assigned U.S. patent application entitled "Holster for Charging Pectorally-Implanted Medical Devices" referenced above. In one embodiment, second holder 414 may be selectively positionable relative to shoulder strap 406, as will be discussed below.

In FIG. 9A, second holder 414 carries coil 254, which is coupled to cable 258. Cable 258 extends around the patient's left side and is connected to recharging device 250 in the manner should in FIG. 8A.

Figure 9B:
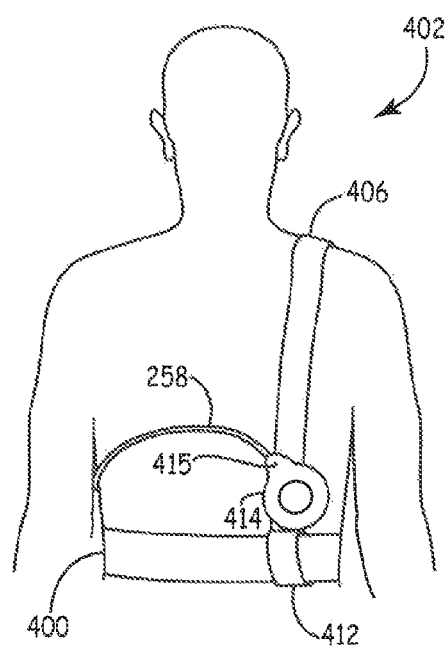
FIG. 9B is a back view of the embodiment of the holster of FIGS. 8A, 8B and 9A.

FIG. 9B is a back view of the embodiment of the holster of FIGS. 8A, 8B and 9A. In FIGS. 8A, 8B, and 9A, like elements are designated with the same numeric identifiers. In FIG. 9B, shoulder strap 406 is shown positioned over the patient's right, rather than left, shoulder in a manner that corresponds to that shown in FIG. 8B. Loop 412 may be slid along torso strap 400 to further adjust the lateral position of second holder 414. In this embodiment, second holder 414 carries coil 254, which is coupled to cable 258. Cable 258 encircles the patient's left side in the manner shown in FIG. 8B.

In a preferred embodiment, coils 252 and 254 are carried within coil holders 410 and 414. The position of coils relative to a patient's torso is highly adjustable. In particular, the lateral (i.e., horizontal) position of coils is adjusted by positioning shoulder strap 406 relative to torso strap 400. In one embodiment, this is accomplished by slidably positioning loops 408 and 412 along torso strap 400. In addition, the height of coil holders 410 and 414 may be adjusted along shoulder strap 406 to accommodate an implant that is located above a patient's waistline. The position of first and second holders 410 and 414 may be adjusted so that coils 252 and 254 will share a same major axis when the coils are carried by the holders. Moreover, the position of holders may be adjusted so that this major axis substantially coincides with a major axis of secondary coil of an IMD implanted within patient 402. This is as shown in FIGS. 4A, 4B, and 5. This allows for efficient recharging of an IMD that is located at a deep-implant location within patient 402.

Figure 10:
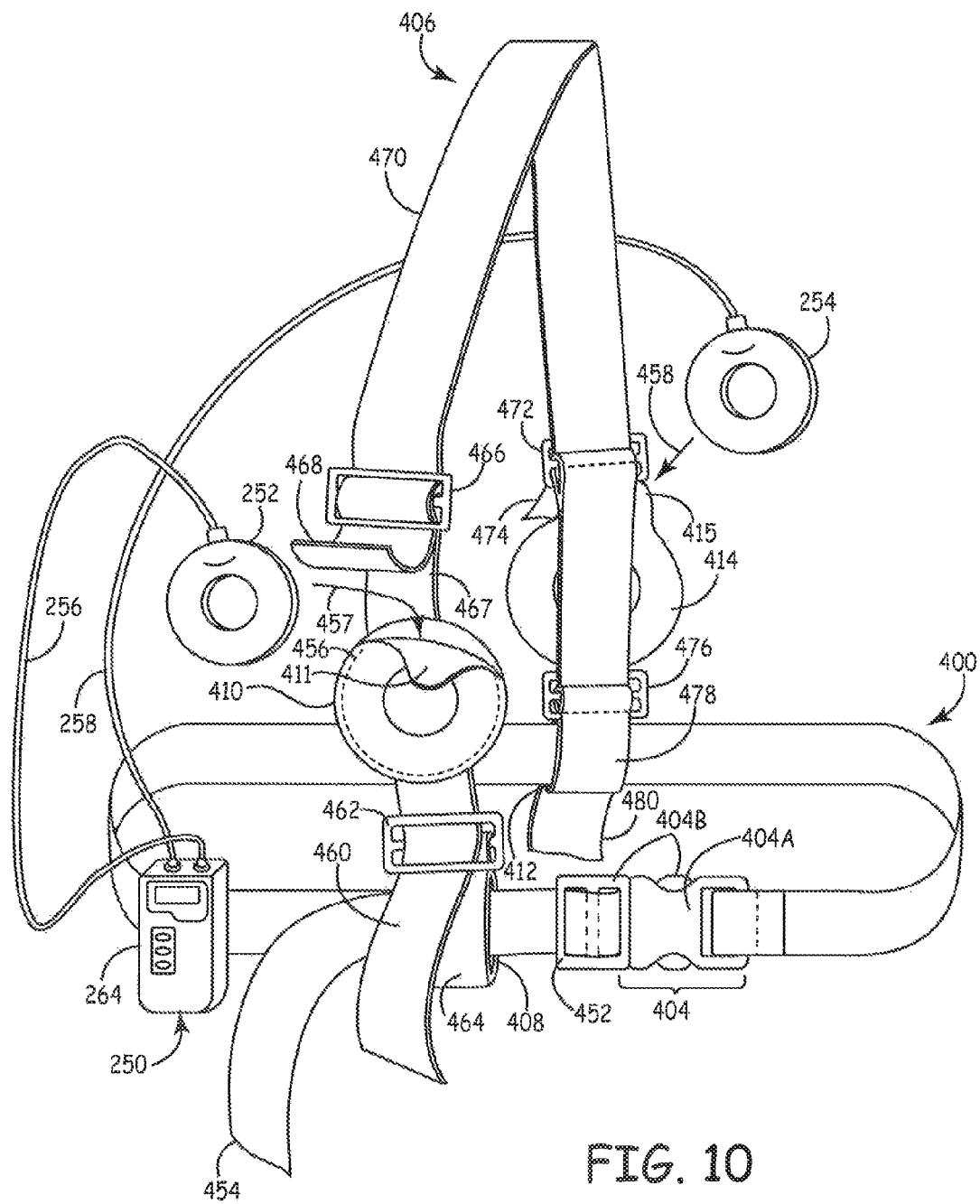
FIG. 10 is a perspective view of a holster according to the embodiment of FIGS. 8A-9B.

FIG. 10 is a perspective view of a holster according to the embodiment of FIGS. 8A-9B. In FIGS. 8A-10, like elements are designated with the same numeric identifiers. Torso strap 400 is shown coupled to a fastener 404. Fastener 404 of the illustrated embodiment includes a female portion 404A that receives and engages a male portion 404B. Male portion 404B includes an adjuster 452 through which end 454 of torso strap 400 is threaded. The length of torso strap 400 is adjusted according to the girth of patient 402 by pulling on end 454.

Shoulder strap 406 engages belt via two slidable loops 408 and 412. Shoulder strap 406 includes first and second holders 410 and 414. In the illustrated embodiment, coil holders 410 and 414 are fashioned by affixing multiple layers of fabric together as by one or more rows of stitching 456. This forms a pocket that may be accessed by grasping one of tabs 411 and 415 to spread the corresponding pocket. For instance, FIG. 10 illustrates tab 411 folded back to expose the pocket of first holder 410. A similar pocket is provided by second holder 414. The pocket is sized to receive one of coils 252 and 254. For instance, coil 252 may be inserted into first holder 410, as indicated by arrow 457. Similarly, coil 254 may be inserted into second holder 414, as indicated be arrow 458.

In one embodiment, shoulder strap 406 includes several adjusters to adjust the length of shoulder strap to fit the length of a patient's torso, as well as to adjust the position of first and second holders 410 and 414, respectively, relative to shoulder strap 406. For instance, adjuster 462 is provided to adjust the height of coil holder 410. In particular, a middle bar of adjuster 462 is coupled to a strap 464 that is folded to provide loop 408. Adjuster 462 further includes two slots through which strap 460 is threaded. By adjusting the position of strap 460 relative to adjuster 462 (e.g., by pulling on end of strap 460), the height of first holder 410 can be adjusted downward or upward relative to torso strap 400.

A similar adjuster 466 is provided to adjust the length of shoulder strap 406. Adjuster 466 includes a middle bar that is coupled to a strap 467 of holder 410. Adjuster 466 includes slots through which an end 468 of an intermediate strap 470 is threaded. By adjusting the position of strap 470 relative to adjuster 466, the length of intermediate strap 470 may be altered to meet a patient's torso length. Alternatively, or additionally, an adjuster 472 may be provided having slots that receive another end 474 of intermediate strap 470 in a manner similar to that shown for adjuster 466. Adjusting end 474 relative to the position of adjuster 472 likewise adjusts the length of intermediate strap 470 to the length of a patient's torso.

Yet another adjuster 476 may be provided that is similar to adjuster 462. That is, adjuster 476 includes a middle bar that is coupled to a strap 478 that is folded to provide loop 412. Adjuster 476 further includes two slots (not visible in FIG. 10) that receive strap 480. By adjusting the position of strap 480 relative to adjuster 476 (e.g., by pulling on an end of strap 480) the position of second holder 414 may be adjusted relative to torso strap 400.

The embodiment of FIG. 10 provides a highly adjustable system that may be used to optimally recharge a rechargeable power source carried by an IMD when the IMD is situated at a deep-implant location within a patient's body. The length of torso strap 400 may be altered via adjuster 452 to fit a patient's girth. The position of coils 252 and 254 may be adjusted laterally (e.g., horizontally) relative to a person's torso by sliding loops 408 and 412 of shoulder strap 406 along torso strap 400. The height of coils may also be positioned vertically via adjusters 462, 466, 472, and 476 in a manner discussed above. These adjusters also allow the length of intermediate strap 470 to be adjusted to fit the length of a patient's torso. In this manner, each of coils 252 and 254 may be adjusted in each of two dimensions so that the coils may be aligned to share a major axis which, in one embodiment, intersects with a center of an IMD implanted within the patient. Optimally, the shared major axis substantially coincides with a major axis of the IMD in the manner illustrated in FIGS. 4A and 4B.

The embodiments discussed above contemplate a system that utilizes two pancake coils that are driven separately by respective ports of a recharging device such that a current having the same amplitude, frequency, and phase are generated in each of the coils. Another alternative embodiment utilizes a pair of circular coils having the same number of turns, the same diameter, and that are positioned along a common axis. The coils are electrically connected in series such that a current flowing in one of the coils also flows in the other coil.

Figure 11A:
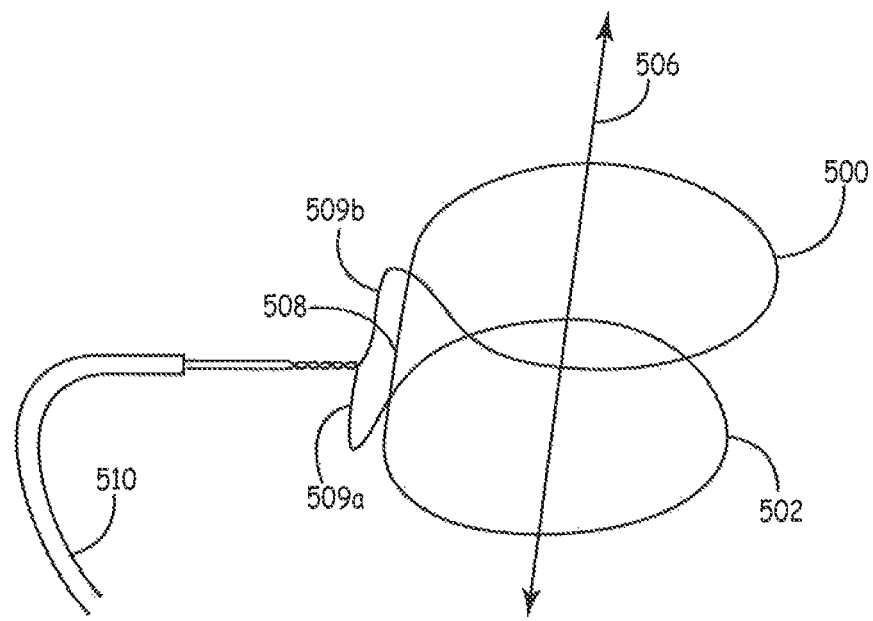
FIG. 11A is a circuit diagram illustrating a pair of in-series coils.

FIG. 11A is a circuit diagram illustrating a pair of in-series coils. The coils are coupled in series with one another via an intermediate conductor 508 such that the same current generated in coil 500 will likewise be generated in coil 502. Conductors 509A and 509B are coupled to, or integral with, coils 502 and 500, respectively. Conductors 509A and 509B are carried back to, and are coupled with, a recharging device via cable 510. This allows the recharging device to drive the in-series coil pair with a current.

Before continuing, it is noted that the foregoing discussion refers to various conductors 508, 509A, and 509B, as well as coils 500 and 502 as though they are formed of different conductors. These structures are, in one embodiment, formed of the same conductor (e.g., wire) that is shaped into a configuration similar to that shown in FIGS. 11A and 11B. The reference to these various conductors is for ease of description only, and it is therefore to be understood that all of the referenced conductors may be integral to one another.

In one embodiment, coil 500 lies in a first plane that is substantially parallel to a second plane in which coil 502 lies. In a more specific embodiment such as that shown in FIG. 11A, the two coils share a major axis 506. As discussed above, a major axis is an axis that intersects the midpoint of the coil and that is also perpendicular to a plane in which the coil lies.

Figure 11B:
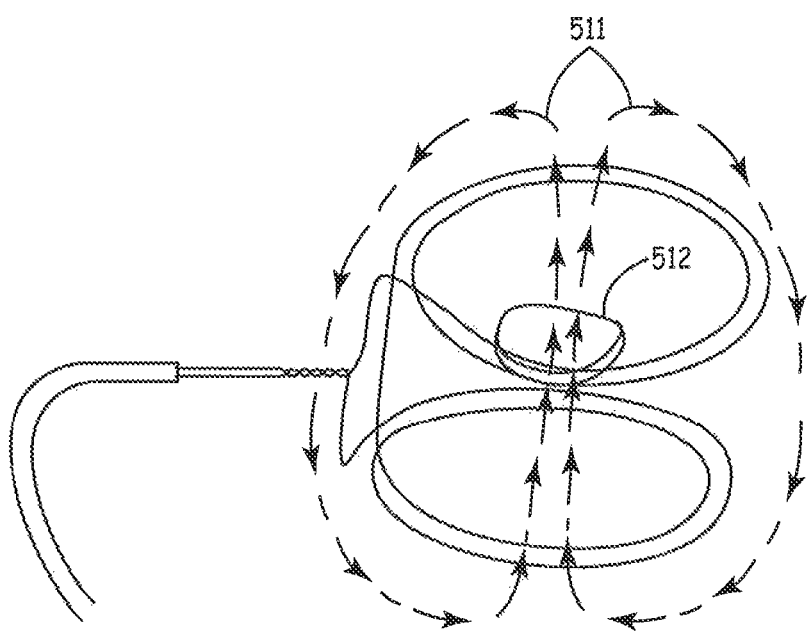
FIG. 11B illustrates in-series coils that are similar to those shown in FIG. 11A but that each include multiple turns.

FIG. 11B illustrates in-series coils that are similar to those shown in FIG. 11A, except that each of the coils includes two turns. It will be understood that for an in-series coil pair, each of the coils may include any number of turns, as long as both coils are the same. FIG. 11B further illustrates flux lines 511 that are produced by the coils when a current is flowing in the counter-clockwise direction in both coils. A current may instead be generated in the opposite direction, if desired.

IMD 512 is located between the two coils. In one embodiment, a major plane of the IMD (that is, a plane intersecting the IMD and which is parallel to the largest surface of the IMD) is substantially parallel to the first and second planes in which the first and second coils, respectively, lie. IMD 512 may be located at an approximate mid-point between the two coils, or at some other point between the two coils. In this manner, a secondary coil that is carried by, and lies in the major plane of, the IMD will be optimally positioned to intercept flux lines 511 so that an efficient recharge session may be conducted.

Figure 12A:
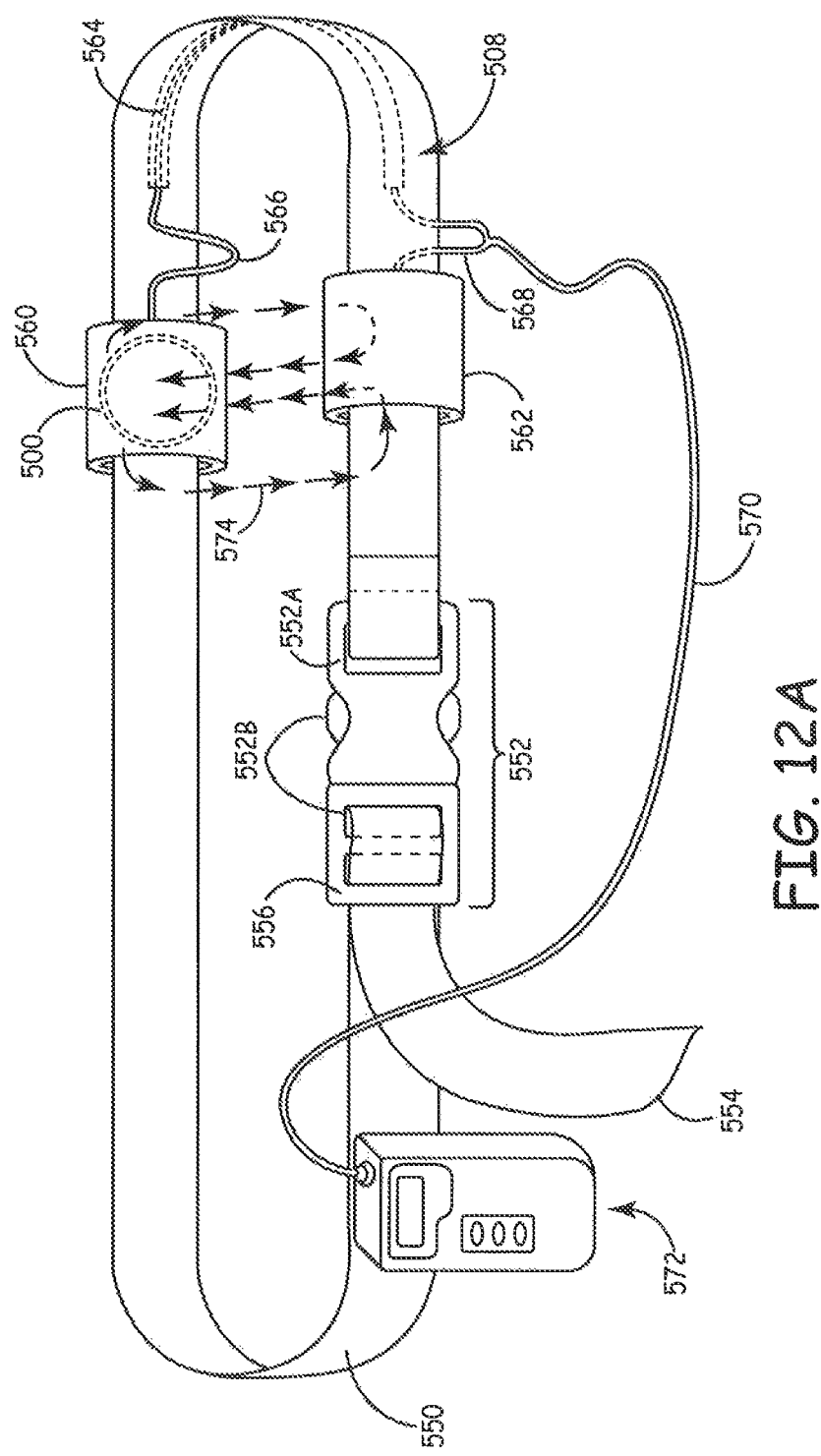
FIG. 12A is a perspective view of one embodiment of a torso strap that may be employed with an in-series coil configuration such as that shown in FIGS. 11A and 11B.

FIG. 12A is a perspective view of one embodiment of a torso strap 550 that may be employed with an in-series coil configuration such as that shown in FIGS. 11A and 11B. Torso strap 550 is adapted to encircle a torso of a patient. Torso strap 550 includes a fastener 552 used to retain the belt around the patient's torso. In the illustrated embodiment, fastener 552 is a buckle that includes a female portion 552A that engages a male portion 552B, although any other type of fastener may be utilized, including a buckle, hook-and-loop strips, hook-and-eye mechanisms, snaps, ties, buttons, and so on.

In the illustrated embodiment, male portion 552B of fastener 552 includes an adjuster 556. An end 554 of torso strap 550 is threaded through adjuster 556. By adjusting the position of end 554 relative to adjuster 556, torso strap 550 is adjusted to fit the girth of a patient's torso.

Torso strap 550 includes first and second holders 560 and 562 that slidably engage torso strap 550. For instance, each holder may be formed by wrapping a strap of flexible durable material such as nylon, cotton, or leather around torso strap 550 and affixing the strap to itself to form a loop. Each of the first and second holders 560 and 562 carries a respective one of the in-series coils. For instance, coil 500 of FIG. 11A (shown dashed in FIG. 12A) may be carried on, or by, an inner surface of first holder 560. Similarly, coil 502 of FIG. 11B (not visible in FIG. 12A) may be carried on, or by, an inner surface of second holder 562.

Coils may be affixed to, or otherwise carried on, a respective holder in a number of ways. For instance, a coil may be held in place on a surface of a holder, or may instead be retained between multiple layers of fabric of a holder using multiple rows of stitching, adhesive, or some other fastening mechanism.

The in-series coils 500 and 502 are coupled to one another by various cable portions 564, 566, and 568. Cable portions 564 and 566 carry intermediate conductor 508 to, and conductor 509B (FIG. 11A) from, coil 500. Likewise, cable portion 564 carries intermediate conductor 508 to coil 502 (not visible), which is on an inner surface of holder 562. Cable portion 568, which is an extension of cable 564, carries conductor 508 to, and conductor 509A (FIG. 11A) from, coil 502. Cable 570 carries conductors 509A and 509B back to recharging device 572. As discussed above, all of these conductors may, in fact, be part of, or formed from, the same conductor (e.g., the same wire) and referencing these various conductor structures is for ease in understanding how the in-series coils 500 and 502 are carried by torso strap 550.

Cable portion 564 is carried in a fixed manner on torso strap 550. For instance, this cable portion 564 may be held in place between fabric layers via rows of stitching. Alternatively, cable portion 564 may be affixed in place with adhesive, or using any other suitable manner.

In one embodiment, cable portions 566 and 568 are provided as extension of cable 564, and are left unattached to the torso strap to allow first and second holders 560 and 562 to move laterally (i.e., horizontally) along the front and back of torso strap 550. This allows the position of coils 500 and 502 to be adjusted laterally. By adjusting the position of coil holders 560 and 562 in this manner, and by further adjusting the height of torso strap 550 around a patient's torso, the coils may be aligned so that they share a major axis, and that this shared major axis intersects an implanted IMD. Optimally, the shared major axis intersects a major axis of the secondary coil of the IMD.

Cable 570 connects coils 500 and 502 and intermediate conductor 508 to a recharging device 572. This recharging device may be fastened to torso strap 550 using a belt clip, a holder such as holder 264 of FIG. 6, or by some other fastening mechanism. During a recharge session, recharging device 572 generates a current in coils 500 and 502 so that flux lines 574 are produced. These flux lines will intersect an IMD that is located between coils 500 and 502 to efficiently recharge a device residing at a deep-implant location.

FIG. 12B is a perspective view of an alternative embodiment of the torso strap shown in FIG. 12A. In FIGS. 12A and 12B, like elements are identified with like numeric designations. In this embodiment, two coil holders 580 and 582 are provided. Coil holder 580 carries pocket 584, and coil holder 582 carries a similar pocket 586 (shown dashed). The pockets 584 and 586 are each sized to receive a coil having some selected maximum diameter. The pockets can thereby receive coils of this maximum diameter, or coils having a smaller diameter. For instance, pocket 584 is shown carrying coil 588 and pocket 586 carries coil 590. In one embodiment, coils 588 and 590 are the same size and will also have the same number of turns and electrical properties. In one embodiment, connectors 589 and 591 are provided so that coils of different sizes may be removably coupled to cable portions 566 and 568.

In another embodiment, the entire coil assembly is removably coupled to torso strap 550. In this embodiment, cable portion 564 is made to be removably affixed to torso strap 550, as by a plastic groove included on the inner surface of torso strap 550 that is sized to receive cable portion 564, as by allowing it to snap into position in the groove. Alternatively, hook-and-loop fastener strips, hooks, ties, or some other coupling mechanism may be used to affix cable portion 564 to the inner surface of torso strap 550. In this manner, coils 588 and 590 may be selected based on a desired coil diameter.

The foregoing figures provide various embodiments of torso straps and/or shoulder straps for retaining the first and second coils in place relative to a patient's body. It will be understood that many other embodiments are possible within the scope of the current invention.

Figure 13A:
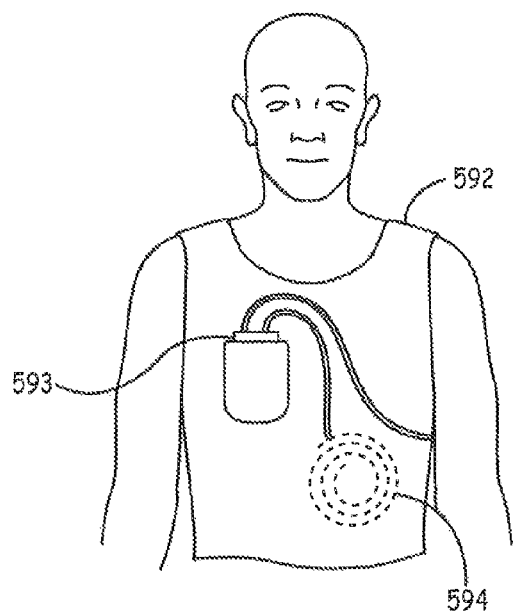
FIGS. 13A and 13B are a front and back view, respectively, of a patient who has donned a garment that covers the chest and torso according to one embodiment.
Figure 13B:
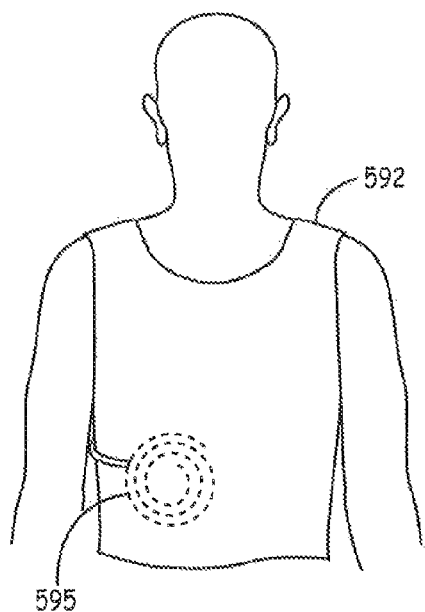

FIGS. 13A and 13B are a front and back view, respectively, of a patient who has donned a garment 592 that covers the chest and torso. This garment may be a shirt, sweater, vest, and so on. This garment carries a first coil 594 (shown dashed) that has been affixed, or otherwise supported, by garment 592. For instance, the coil may be stitched into the fabric, attached via adhesive or any other fastening means known in the art, supported by a pocket, etc. Coil may be provided on the underside of the garment (as indicated by dashed lines) to allow for better coupling with the patient's skin. Coil 594 has been coupled to a recharging device 593, which may be supported by a pocket of the garment. A second coil 595 (shown dashed), which is likewise coupled to recharging device 593, is carried on the backside of the garment, as shown in FIG. 13B. The two coils are arranged so that they are on opposing sides of the body. In one embodiment, the coils share a major axis.

A garment such as shown in FIGS. 13A and 13B may be adapted to carry the coils anywhere on the garment. For instance, the coils may be carried on the sides of the garment so that they are located substantially under the arms of the patient. This configuration may be selected to recharge an IMD that has a secondary recharge coil that lies in a plane substantially parallel to the sides of the patient's torso. Alternatively, the coils may be carried at a higher or lower position on the garment based on the location of the IMD within the patient. In one embodiment, the entire garment could include hook-and-loop fastening strips that are provided to receive opposing strips on the coils so that the coils may be selectably repositioned anywhere on the garment. This allows one garment design to be suitable for use by different patients having different implant locations.

Figure 13C:
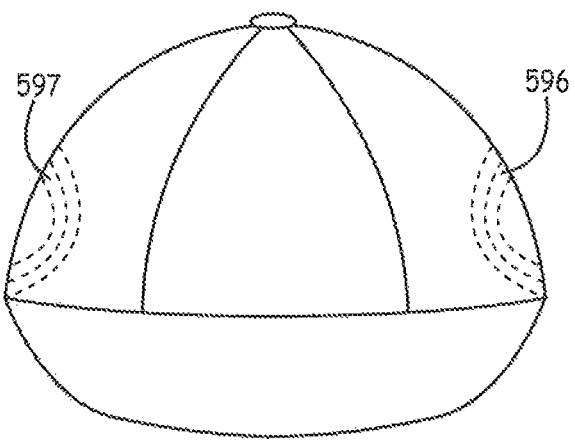
FIG. 13C is a view of another embodiment adapted to carry coils positioned around the patient's head.

FIG. 13C is a view of another embodiment adapted to carry coils positioned around the patient's head. In this embodiment, a cap carries coils 596 and 597 (shown dashed), which may be affixed to the cap in any manner known in the art, including using those mechanisms mentioned above. The coils may be positioned on any two opposing sides of the cap (e.g., front and back, left and right, etc.). These coils may be provided on the underside of the cap to provide better coupling to the patient. Other headwear may be used instead of a cap to carry the coils, including any type of hat, or a headset of the type that may be used to listen to portable audio devices. This embodiment is suitable to recharge an IMD implanted within a patient's head.

Figure 13D:
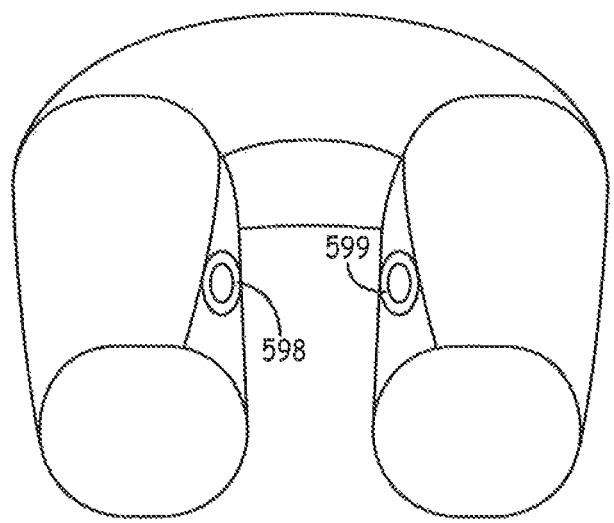
FIG. 13D is a view of an embodiment adapted to be positioned proximal to a patient's neck.

FIG. 13D is a view of an embodiment adapted to be positioned proximal to a patient's neck. This neckwear may be similar to inflatable braces used by travelers to aid in relaxation during a long trip. The neckwear may be formed of foam or any other material that is capable of holding its shape yet is comfortable during use. The neckwear consists of a support member having an opening that receives a person's neck. When the neck is so positioned with the opening, the neckwear surrounds the neck around the back and sides of the neck. Coils 598 and 599 are carried on the inner surface of the opening so that they are proximal to the sides of the neck. The coils are adapted to most efficiently recharge an IMD having a secondary coil that lies in a plane substantially parallel to the sides of the neck.

A variation of the neckwear provides an opening that opens on a first side of the neck so that when the neckwear is donned, it surrounds the neck on the front, back, and the second side of the neck. The coils may then be positioned proximal to the front and back of the neck to recharge an IMD having a secondary coil that is located in a plane substantially parallel to the front and back of the patient's neck.

FIG. 13F is a side perspective view of an embodiment that carries a first coil 601 on a support structure 600 on which the patient lies and a second coil 604 carried by an item 603 that covers the patient. For instance, the support structure 600 that carries the first coil may be a mattress pad, a blanket, a sleeping bag, a sofa cushion, or any other structure on which the patient may lie. The item that covers the patient may be a blanket, sheet, or any other item adapted to be positioned over the patient. Coils 601 and 604 may be aligned so that they share a major axis. Further, they may be aligned so that this major axis intersects, or even shares a major axis with, an implanted IMD within the patient. Current is then generated in the coils by recharging device 602.

In one embodiment, support structure 600 and item 603 may be incorporated into a single structure. For instance, a sleeping bag may be provided that carries the coils on opposite sides of the bag (e.g., top and bottom, left and right side, etc.) When the patient is inside this structure, the coils are then substantially aligned on opposing sides of the patient's body. The configuration of the structure is selected based on the patient's particular implant scenario.

Figure 13G:
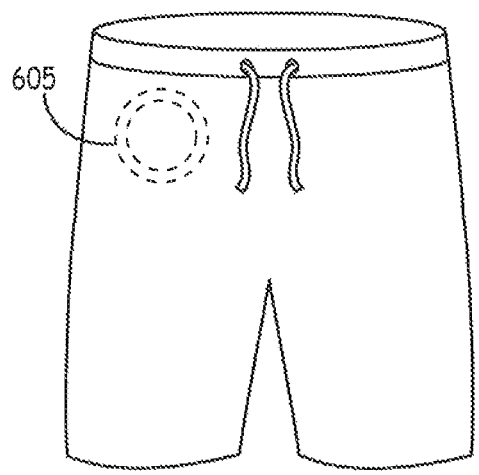
FIG. 13G is an embodiment that carries the coils on a garment to be donned on a lower portion of the patient's torso.

FIG. 13G is an embodiment that carries the coils on a garment to be donned on a lower portion of the patient's torso. For instance, the garment may be pants, shorts, a skirt, and so on. In this example, coil 605 (shown dashed) is shown positioned on the front of the garment. A similar coil (not shown) is positioned on the back of the garment. In one implementation, this second coil is located so that it substantially shares a major axis with coil 605. The coils are thereby provided for use with an IMD implanted in a lower portion of the patient's torso. If desired, the coils may be positioned in the leg portion of the garment to recharge an IMD implanted in the patient's leg.

The various embodiments discussed above may be best suited for an application wherein the secondary coil of the IMD is located within a plane that is roughly parallel to the planes that carry the coils. However, when the secondary coil of the IMD is in a plane that is angled, the foregoing embodiments may not be as effective in recharging a power source carried by the IMD. This is because most of the flux lines generated by embodiments such as those discussed above will not be intercepted by a secondary recharge coil that is associated with, and substantially in the plane of, the IMD.

Figures 14A, 14B:
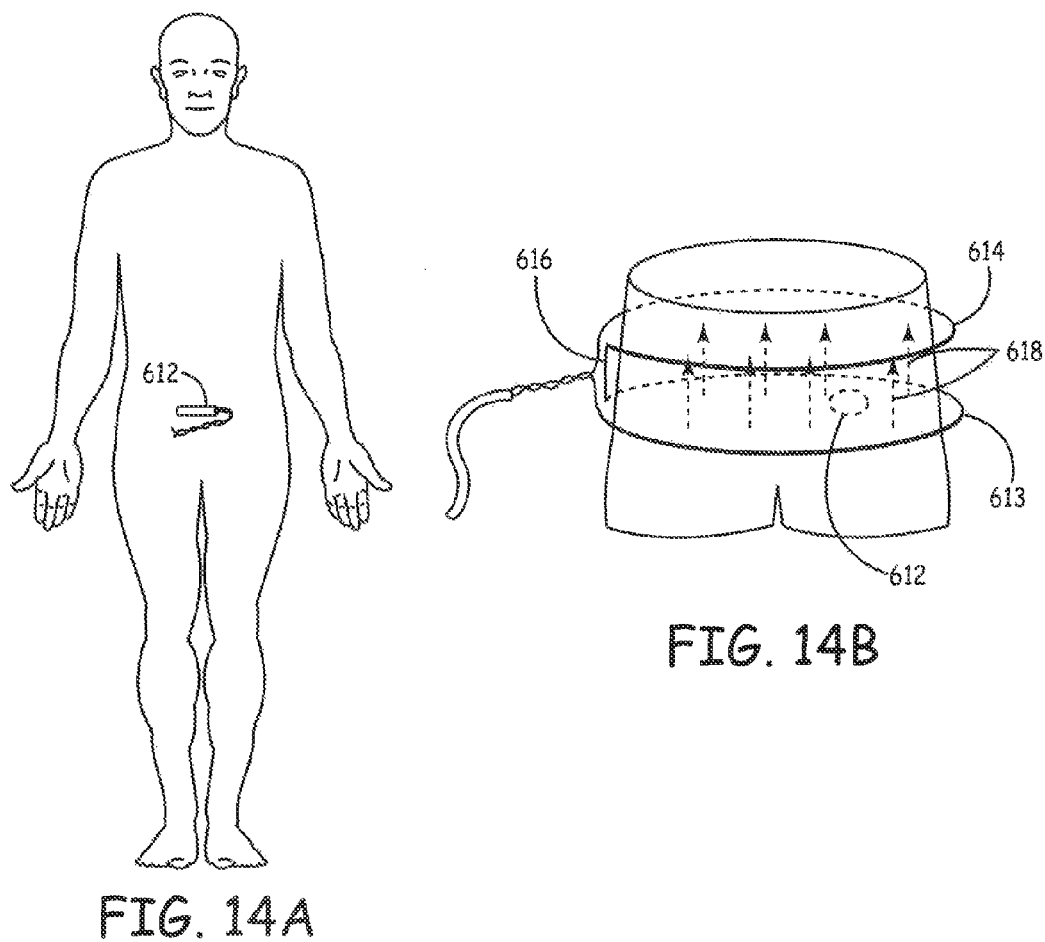
FIG. 14A is a front view of a patient in which an Implantable Medical Device is implanted in an angled configuration.
FIG. 14B illustrates an embodiment of the current invention that is adapted to recharge an Implantable Medical Device that is angled in a manner similar to that shown in FIG. 14A.

FIG. 14A is a front view of a patient in which an IMD 612 is implanted in an angled configuration. The IMD is located within a plane that is substantially perpendicular to the front, the back, and both sides of the patient's torso. In this type of scenario, the embodiments discussed above may result in diminished recharge efficiency.

FIG. 14B illustrates an embodiment of the current invention that is adapted to recharge an implant that is angled in a manner similar to that shown in FIG. 14A. This embodiment utilizes two coils that encircle a patient's torso to perform recharge of the angled implant. A first coil 613 and a second coil 614 are wrapped around the patient's torso. The coils may, but need not, be electrically connected in series via an intermediate conductor 616. This in-series configuration is similar to the orientation of the two in-series coils shown in FIGS. 11A and 11B. A counter-clockwise current induced in the coils will generate flux in the direction shown by flux lines 618. This flux optimally intersects a plane in which IMD 612 lies, which is substantially perpendicular to the flux. Thus, an efficient recharge session may be conducted for a device that is angled within the patient.

Figure 15:
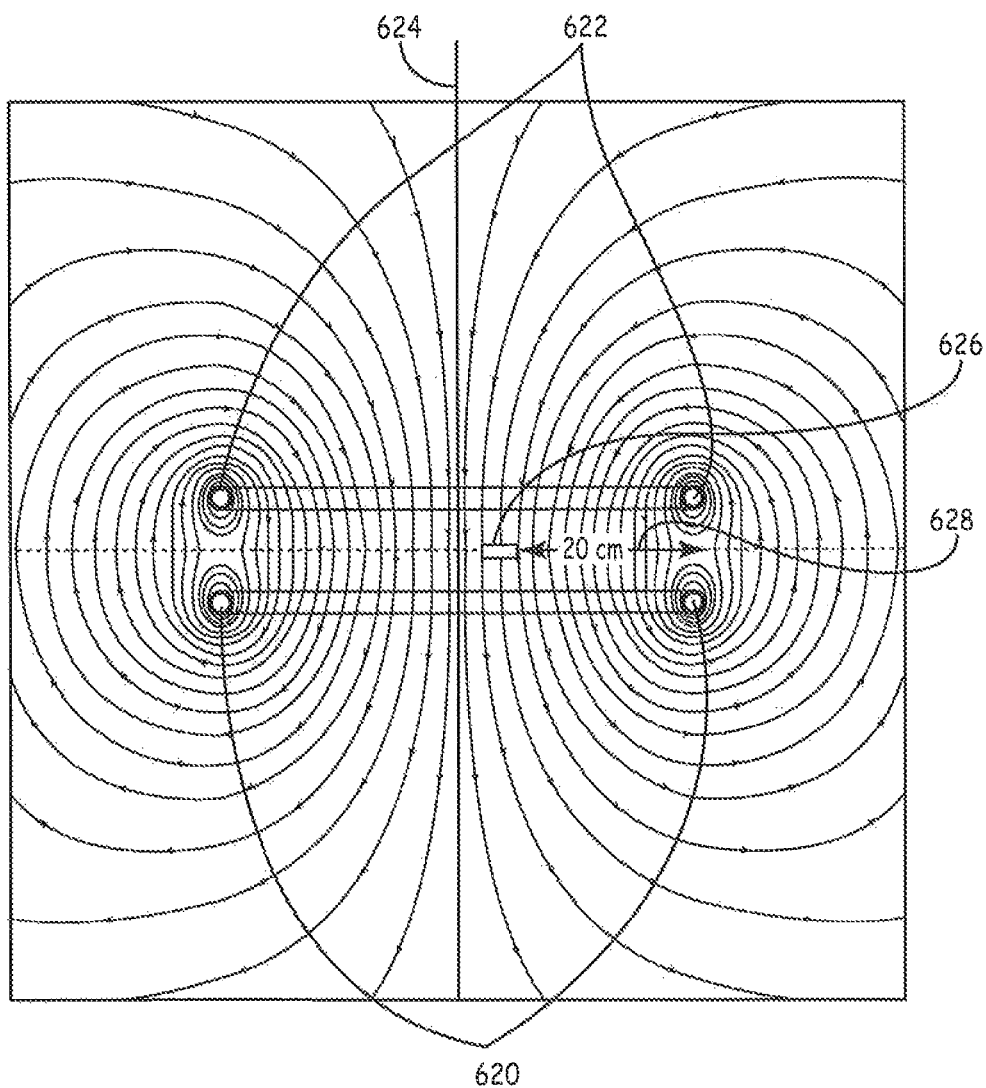
FIG. 15 is a flux diagram illustrating flux lines generated by a pair of coils that encircle a portion of the patient's body.

FIG. 15 is a flux diagram illustrating flux lines generated by a pair of coils 620 and 622 (each shown in cross-section) that may be conceptualized as encircling a patient's torso in a manner similar to that shown in FIGS. 14A and 14B. In this diagram, these coils substantially share a major axis 624. As discussed above, a major axis intersects a center of the coils and is perpendicular to the plane in which the coil lies.

This example represents the situation wherein major axis 624 parallels the length of the patient's spine, with the patient being encircled by the coils. The front, back, and sides of a patient's torso would also be generally parallel to axis 624. The flux lines of FIG. 15 are generated by two coils that are 10 cm apart having a diameter of 50 cm and including 20 turns. In one embodiment, the coils are formed of copper litz wire, type 20-26 American Wire Gauge (AWG). When a current of 1 mA is induced in the coils 620 and 622, a flux density of 305 nT is generated at a location 626 that is equidistant from each coil and that is roughly 5 cm from axis 624. This represents an implant depth of about 20 cm, as indicated by arrow 628.

As is apparent from the foregoing, for an implant depth of about 20 cm, two 20-turn coils having a diameter of 50 cm and that are positioned around a patient's waist in the manner represented by FIG. 15 generate the same flux density as two 100-turn coils having a diameter of 10 cm that are positioned on the front and back of a patient's torso in the manner represented by FIG. 5.

Figure 16:
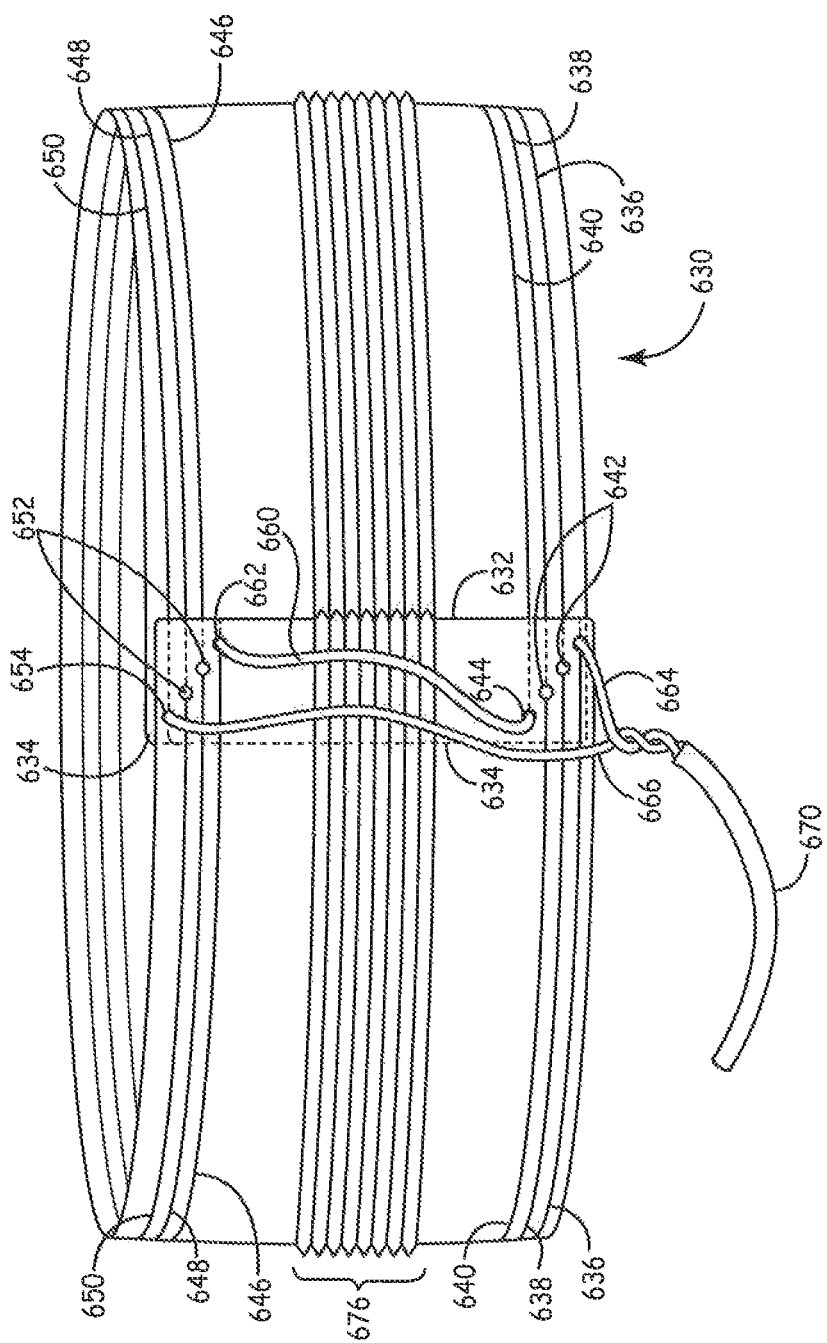
FIG. 16 is one embodiment of a system that provides two in-series coils that encircle a patient's torso.

FIG. 16 is one embodiment of a system that provides two in-series coils that encircle (that is, wrap around) a patient's torso in a manner similar to that shown in FIGS. 14A, 14B, and 15. A belt 630, which may also be described generally as a torso strap, is formed of a durable strip of material such as nylon, cotton, leather or some type of fabric. Belt 630 is sized to fit around a patient's torso when a first end 632 of the belt 630 is positioned to overlap the other end 634 (shown dashed) in the manner illustrated in FIG. 16.

Belt 630 carries one or more conductors along a lower edge, and an equal number of conductors along an upper edge. For instance, in the illustrated embodiment, three conductors 636, 638, and 640 extend approximately the entire length of belt along the lower edge. Similarly, conductors 646, 648, and 650 extend approximately the entire length of belt 630 along the upper edge. As one example, these conductors may be formed of copper litz wire, type 20-26 AWG, although other types of conductors may be used in the alternative. These coils may be affixed to the belt using stitching, adhesive, or some other suitable mechanism.

At end 632, conductors 638 and 640 are each electrically coupled to an electrical via 642. Each of the vias 642 extends through to the underside of belt 630 and electrically couples to, or is integral with, a respective male contact member (not visible in FIG. 16) that is formed of an electrically conductive material. An additional via 644 is provided that electrically couples to, or is integral with, an additional male contact member in the manner discussed above.

At end 634 of belt, each of conductors 636, 638, and 640 is electrically coupled through to a female fastening member that is on the front side of belt 630 (not visible in FIG. 16). When belt 630 is configured in a loop as to encircle a patient's torso in the manner shown in FIG. 16, each of the female contact members on the front side of end 634 of belt 630 may be electrically coupled with a corresponding one of the male contact members provided at the underside of the belt at end 632. For instance, via 642 of conductor 638 extends through belt 630 to a male contact member on the underside of belt which is provided to couple to a female contact member of conductor 636 that is located at end 634. Similarly, via 642 of conductor 640 extends through belt to a male contact member which is adapted to mate with a female contact member of conductor 638. Finally, via 644 extends to a male contact member, which couples to a female contact member of conductor 640. In this way, the three conductors 636, 638, and 640 are electrically coupled in a serial manner to form a three-turn coil when the electrical contacts are made between the male contact members located on the underside of end 632 and the female contact members on the front side of end 634.

In a similar manner to that described above, at end 632, conductors 648 and 650 are each electrically coupled to a respective one of vias 652. Each of the vias 652 extends through to the underside of belt 630 and electrically couples to, or is integral with, a respective male contact member that is formed of an electrically conductive material. An additional via 654 is provided that electrically couples to, or is integral with, an additional male contact located on the underside of the belt in the manner discussed above.

At end 634 of belt, each of conductors 646, 648, and 650 is electrically coupled to a female fastening member that is on the front side of belt 630. Each of the female contact members at end 634 of belt 630 is provided to electrically couple with a corresponding male contact member that is located at end 632 of belt 630. For instance, via 652 of conductor 648 extends to a male contact member which is provided to couple to a female contact member of conductor 646 located at end 634. Similarly, a via 652 of conductor 650 extends to a male contact member which is adapted to couple to a female contact member of conductor 648. Finally, via 654 electrically couples through a male contact member to a female contact member of conductor 650. In this way, the three conductors 646, 648, and 650 are electrically coupled in a serial manner to form a three-turn coil when the electrical contacts are made between the male contact members located on the underside of the belt at end 632 and the female contact members located on the front side of the belt at end 634.

Finally, a conductor 660 is provided to electrically couple the electrical via 644 with an electrical via 662, thereby electrically coupling the two coils in series. This results in an in-series coil pair that encircles the patient's torso. The in-series pair may be coupled to a recharging device (not shown in FIG. 16) through conductors 664 and 666 that are carried in cable 670. A recharging device may be used to generate a current in the in-series coil pair to induce magnetic flux lines that are substantially parallel to the spine of a patient donning the device. This magnetic field more optimally induces a current in a secondary recharge coil carried within an IMD of an angled device, such as one that lies in a plane substantially perpendicular to the spine of the person donning belt 630.

In one embodiment, belt has an intermediate portion 676 of belt that is formed of a material that is expandable and contractible to allow a user to select the distance between the two coils. For instance, intermediate portion 676 may be formed of an accordion-like material having folds or pleats. This may be useful when recharging IMDs that are not located directly at a person's waist. For instance, if the IMD is implanted higher in a patient's abdominal cavity, the bottom of belt may be positioned approximately at the patient's waist, whereas the top of the belt may be extended upward by expanding intermediate portion 676 towards the patient's pectoral region. This allows the coils to surround an IMD that is implanted higher in the chest region. Alternatively, the belt may simply be donned at a higher position around the patient's torso.

The embodiment shown in FIG. 16 is designed to fit a torso having a predetermined girth. Belt 630 may be made more versatile by providing multiple sets of male contact members and/or multiple sets of female contact members along the length of conductors 636, 638, 640, 646, 648, and 650.

FIG. 16 illustrates an embodiment wherein the coils are electrically arranged in series and encircle the patient's torso. The current in the coils is generated using a single pair of conductors 664 and 666 that may be coupled to a single port of a recharging device. In an alternative embodiment, the coils need not be in-series, but instead may each be coupled individually to the recharging device via a respective cable. In this type of configuration, belt 630 may be modified to eliminate conductor 660, which arranges the coils in series. Instead, the recharging device will drive the two coils individually, as may be accomplished using two ports. In one implementation, the recharging device will drive the coils so that the current in each of the two coils has the same amplitude, frequency, and phase.

FIG. 16 further illustrates that the turns of the coil need not be co-planar. For instance, conductors 646, 648, and 650 are connected to form a three-turn coil. The turns of the coil are "stacked" one on top of another rather than residing in a same plane as they would if the turns of the coils were concentric. Thus, the three-turn coil may be said to be carried in multiple planes that are substantially parallel to one another and share a same major axis. This major axis is substantially perpendicular to each of the multiple planes that carry the coils, and this major axis further intersects the centers of the turns of the coil. In this embodiment, this major axis would be approximately parallel to a spine of the patient that is donning belt 630.

In accordance with the foregoing, conductors 636, 638, and 640 are connected to provide a first coil that may be described as lying in a first plane. That first plane is one of multiple substantially parallel planes that carry the turns of the first coil, which are stacked one on top of each other. Likewise, conductors 646, 648, and 650 are interconnected to provide a second coil that lies in a second plane, wherein that second plane is one of multiple substantially parallel planes that carry the turns of the coil. The second plane may be described as being substantially parallel to the first plane. When belt 630 is donned by a patient, an IMD that residing in an abdomen or torso region of the patient is situated between the first and second planes. A recharging device coupled to each of the first and the second coils generates a current in the first and the second coils that electromagnetically couples the first and the second coils to a secondary recharge coil to recharge a rechargeable power source of the IMD.

Figure 17:
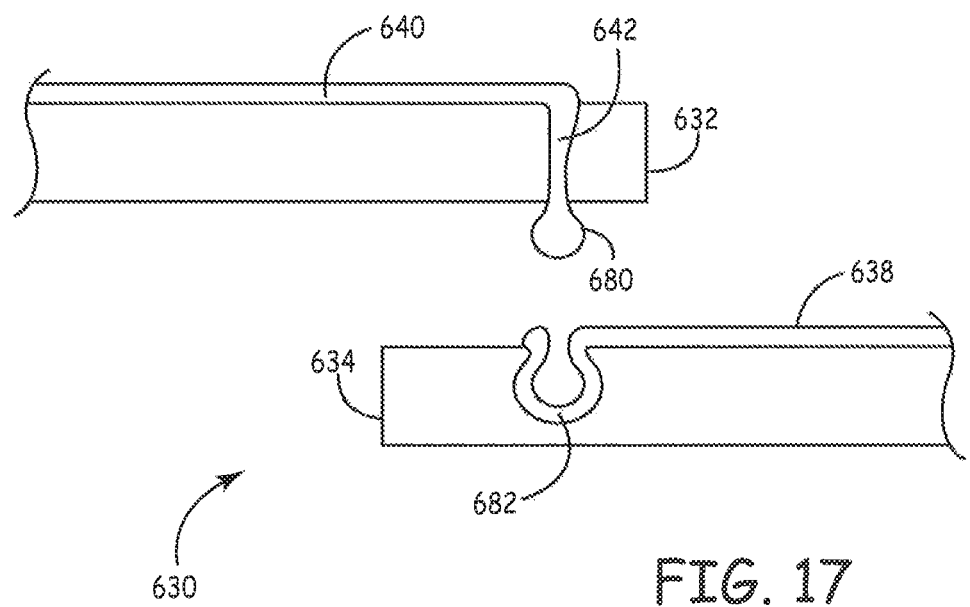
FIG. 17 is a cross-sectional exploded view of the two ends of the belt of FIG. 16 illustrating how these ends overlap when the belt is donned.

FIG. 17 is a cross-sectional exploded view of ends 632 and 634 of belt 630 illustrating how these ends overlap when the belt is donned. In particular, this view illustrates how a conductor at end 632 of the belt 630 is electrically coupled to a conductor at the other end 634 of belt when the belt is donned. In this particular example, conductor 638 at end 632 is shown being coupled to conductor 640 at end 634, although this discussion applies equally to the other conductors of the belt.

As mentioned previously, conductor 640 is electrically coupled to an electrical via 642. This via 642 extends through to the underside of belt 630 and electrically couples to, or is integral with, a respective male contact member 680 formed of electrically-conductive material. Similarly, conductor 638 at end 634 is electrically coupled to a female fastening member 682 that is on the front side of belt 630. When belt 630 is configured in a loop as to encircle a patient's torso in the manner shown in FIG. 16 so that end 632 overlaps with end 634, female fastening member 682 aligns with male fastening member 680. The male fastening member 680 may be snapped into position to engage female fastening member 682, thereby providing mechanical coupling of the two belt ends, and also electrically coupling conductor 638 to conductor 640. In an alternative embodiment, the female fastening member may reside at end 632 and male fastening member may be located at end 634.

In FIG. 17, conductors 638 and 640 are each illustrated as being a raised member that protrudes from the surface of belt 630. This need not be the case. The conductors may be embedded within the fabric or other material that forms belt 630. Moreover, the conductors may reside on the undersurface of the belt to make better contact with a patient's skin, particularly if the belt is worn under clothing. In this case, the coupling of the conductors to the fastening members will be somewhat different, since via 642 will no longer be needed, but a via may be necessary to couple conductor 638 to female fastening member.

Figure 18:
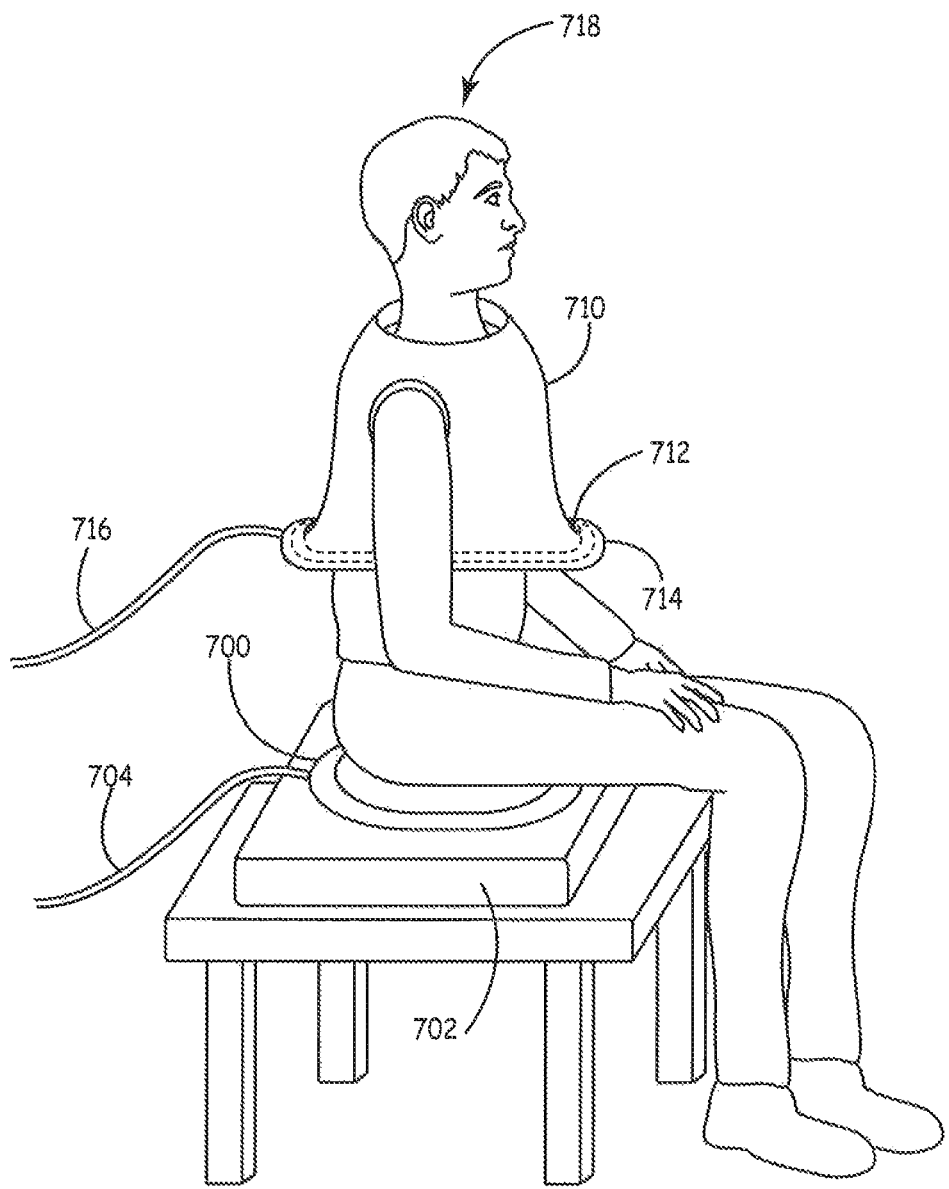
FIG. 18 is another embodiment of a system that provides dual coils for an angled implant.

FIG. 18 is another embodiment of a system that provides dual coils for an angled implant. In this embodiment, a first coil 700 is carried on, or embedded in, a support structure 702 on which the patient is seated. For instance, this support structure may be a cushion 702, a pillow, a chair, a stool, or any other structure. This support structure may be a portable seat cushion that can be carried with the patient and thrown on any chair or stool during a recharge session. This first coil 700 may be coupled to a recharging unit via cable 704.

The system also includes a garment 710 such as a vest that may be donned by sliding it over a patient's head and arms. The vest carries a coil 712 (shown dashed), which in one embodiment has the same number of turns, dimensions, and coil properties as coil 700. The coil 712 may be carried on, or in, a bell-like projection 714 that extends from the bottom of garment 710, as may result in optimal electromagnetic coupling in some situations. In another embodiment, coil 712 may be merely carried around the lower edge of the vest that is substantially parallel to the patient's body rather than bowed away from the body. In either embodiment, the coil may be carried by the garment using stitching, adhesive, hooks, hook-and-loop strips, ties, or any other fastening mechanism that may be used to affix coil 712 to garment 710.

The garment may include means to allow the coil height to be adjustable so that the coil is positioned optimally for the height of the implant within the patient. For instance, garment 710 may include a layer of folded or pleated material that is similar to portion 676 of belt 630 (FIG. 16). In one embodiment, this allows coil 712 to be positioned so that an IMD within patient 718 is approximately midway between coils 700 and 712.

Coil 712 is coupled to a recharging device via cable 716. The recharging device drives the two coils individually, generating current in both coils 700 and 712 so that magnetic flux lines are generated that are approximately parallel to the patient's spine to optimally recharge an IMD that is angled within the patient's body. In one embodiment, the generated current is the same in both coils.

FIG. 18 illustrates that the turns of a coil may be oriented such that some turns are inside of the other turns, rather than being stacked on top of each other, as shown in FIG. 16. For example, one or more turns of coil 700 have a smaller circumference than, and are located within, one or more other turns of the coil 700. The various turns of coil 700 may, but need not, be co-planar. Thus, coil 700 may not only have some turns that are "wrapped inside" the other turns of the coils, but coil 700 may also have some turns that are "stacked" on other turns. All turns of the coil are substantially concentric.

Likewise, in one embodiment, some turns of coil 712 may have a smaller circumference than other turns of the coil. The turns of the coils may, but need not, be co-planar to one another. For instance, because of the shape of bell-like projection 714, an inner turn of coil 712 that has a smaller circumference than another turn of coil 712 may reside in a plane that is farther from coil 700 than the plane that carries an outer turn of coil 712. That is, the turn with the smaller circumference is "above" the turn with the larger circumference. In a different embodiment, the reverse may be true, and a turn of coil 712 with a larger circumference may reside in a plane that is farther from coil 700 than another turn of the same coil with a smaller circumference. That is, the turn with the larger circumference is "above" the turn with a smaller circumference.

The foregoing illustrates that a coil of the current invention may be of any number of turns. The turns may be stacked one on top of the other, and/or the turns may reside one inside the other. The turns may reside substantially in a single plane, as may, but need not, be the case when the turns reside one inside the other, as depicted by coil 700. When the turns of a coil reside in multiple planes, these planes will be substantially parallel to one another.

Figure 19:
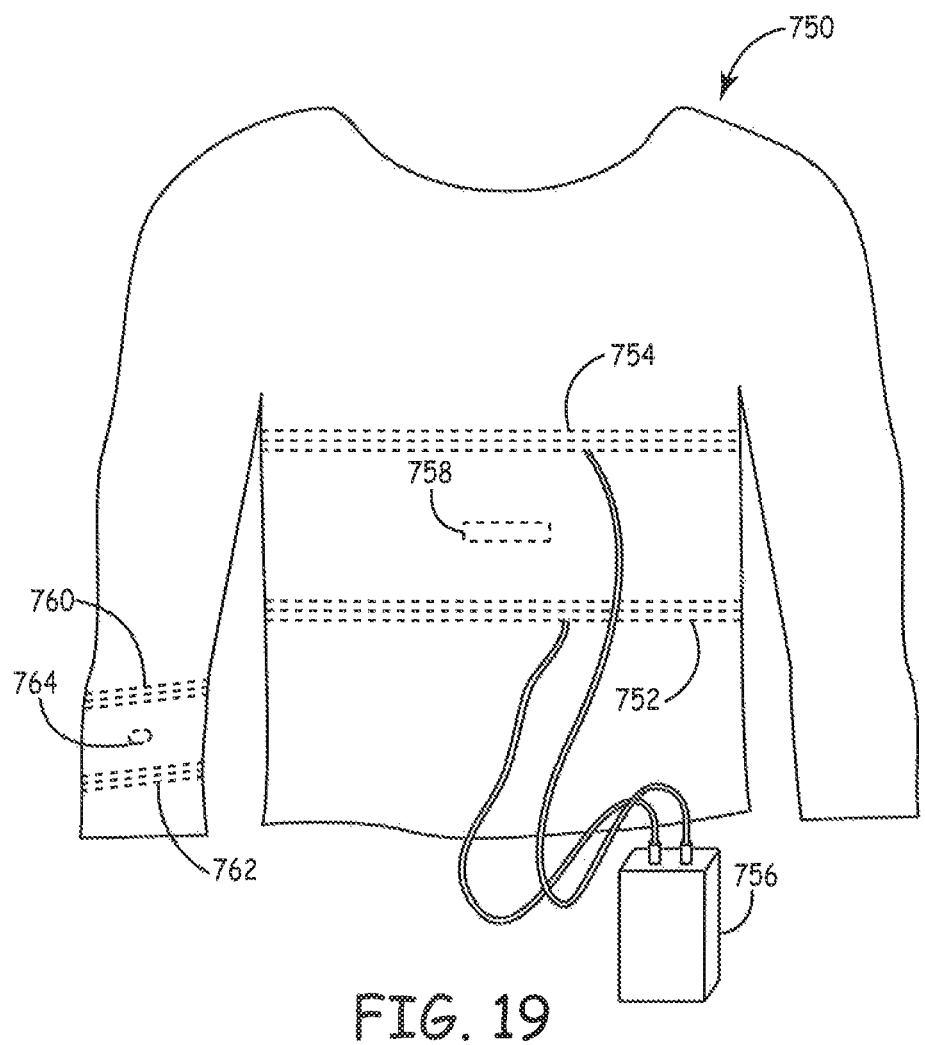
FIG. 19 is another embodiment of a garment having two coils that encircle a portion of the patient's body.

FIG. 19 is another embodiment of a garment 750 having two coils that encircle, or wrap around, a portion of the patient's body. This garment may be any type of shirt, vest, jacket, sweater, or another type of garment to be donned by an upper portion of the patient's body. Coils 754 and 752 (shown dashed) each encircle the patient's torso when the garment is donned, and may be provided on the underside of the garment to allow for better coupling with the patient. They are shown coupled to recharging device 756, which drives the coils individually. An embodiment may be provided that has an intermediate conductor (similar to that shown in FIG. 16) that electrically couples the two coils in series so that they may be driven by a single port of recharging device 756. Resulting magnetic flux lines will couple to a secondary recharge coil of IMD 758 (shown dashed) that is angled within the patient's body.

FIG. 19 further illustrates how the turns of the coils may be "stacked" one on top of another, as was the case in the embodiment of FIG. 16. Thus, the turns of coil 754 are not co-planar, but rather reside in multiple planes that are substantially parallel to one another. A major axis of the coil lies substantially perpendicular to the multiple planes that carry the coil. Likewise, turns of coil 752 are not co-planar, but rather reside in multiple planes that are substantially parallel to one another.

In accordance with the foregoing, first coil 754 may be described as lying in, or being carried by, a first plane, wherein that first plane is only one of multiple planes in which this first coil lies. Likewise, coil 752 may be said to lie in a second plane, which is one of multiple planes in which coil 752 is carried, or lies. The second plane may be described as being substantially parallel to the first plane. When garment 750 is donned by a patient, IMD 758 lying in an abdomen or torso region of the patient is situated between the first and second planes. In a more particular embodiment, a plane carrying a secondary coil of IMD 758 may be substantially parallel to, and may lie between, the first and second planes to result in optimal inductive coupling between the first and second external coils and the secondary coil.

Similar coils may be provided to recharge an angled implant located in other portions of the patient's body. For instance, coils 760 and 762 (shown dashed) may be provided to recharge an angled IMD 764 (shown dashed) located within a patient's arm.

Figure 20A:
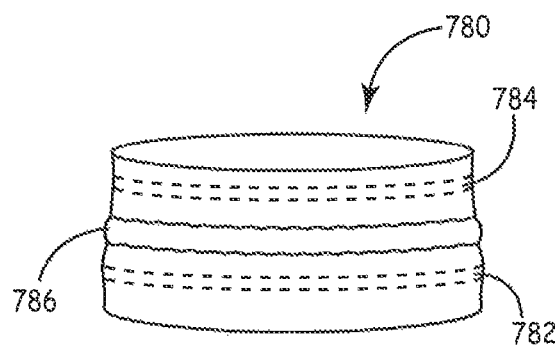
FIG. 20A is a band that carries two coils according to one embodiment.

FIG. 20A is a band 780 that carries two coils 782 and 784 (shown dashed). This band may be sized to fit around a portion of the patient's body in which an IMD is implanted, such as an arm, a wrist, a leg, an ankle, a head, a foot, a neck or any other body part. For instance, this band may be positioned around a patient's head to recharge an IMD implanted within the brain. The band may include an optional elastic portion 786 that is provided to retain the band in a selected position around the desired portion of the body. When in position, the IMD will lie between the two coils.

In a variation of FIG. 20A, headwear may be provided that carries two coils. The coils are configured in a manner similar to that shown in FIG. 20A such that when the headwear is donned, the coils encircle the patient's head. The headwear may be a cap, a hat, a headset that supports the coils so that they encircle the patient's head, or any other type of mechanism worn on the head for supporting the coils in this manner.

Figure 20B:
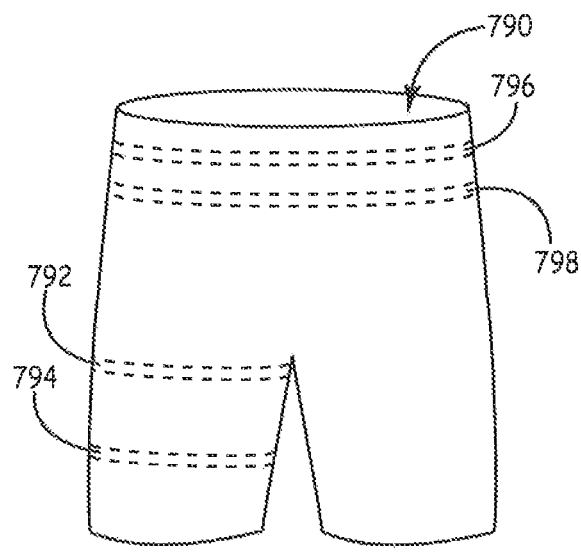
FIG. 20B is a garment to be worn around the lower portion of a patient's torso according to an embodiment.

FIG. 20B is a garment 790 to be worn around the lower portion of a patient's torso according to the current invention.

This garment may be shorts, pants, or any another garment of this nature. The garment includes coils 792 and 794 (shown dashed). When the garment is donned, these coils encircle a portion of the patient's leg for recharging a rechargeable power source of an IMD that is positioned between the two coils. In another adaptation, coils 796 and 798 (shown dashed) may be provided for an IMD located within the torso.

Figure 21:
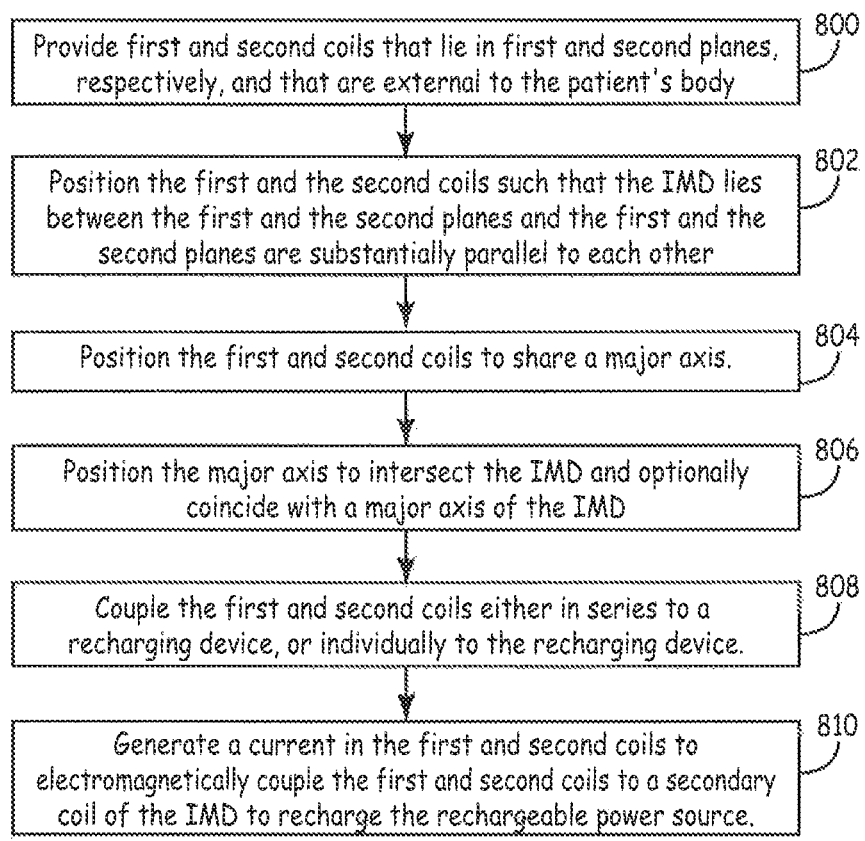
FIG. 21 is a flow diagram of one exemplary method of using the current invention.

FIG. 21 is a flow diagram of one exemplary method for using the current invention. First and second coils are provided that lie in first and second planes, respectively (800). The coils are external to a patient's body. These coils are positioned so that the IMD lies somewhere between the first and second planes and so that the first and second planes are substantially parallel to each other (802). The IMD may lie anywhere between the coils, although best recharge efficiency may be achieved when the IMD is positioned roughly half-way between the coils.

As discussed above, positioning step 802 may involve wrapping the coils around some portion of the patient's body, which may include the head, neck, arm, hand, wrist, chest, torso, leg, ankle, foot, or any other portion. Alternatively, this may involve placing the coils on opposing sides of the patient's body, such as a front and back of a torso, on two sides of the torso, or on any other two opposing surfaces of the patient's body.

The first and the second coils may optionally be positioned so that they share a same major axis (804). Additionally, the major axis may be aligned to intersect the IMD, and even to coincide with a major axis of the IMD, if desired (806). While this may result in a most efficient recharge session, the coils need not be aligned as described in steps 804 and 806 in an alternative embodiment.

In step 808, the first and second coils may then be coupled to a recharging device so that the coils are electrically arranged in-series (e.g., via a same port), or so that the coils will be driven individually (e.g., via different ports). A current is then generated in the first and second coils to electromagnetically couple the first and the second coils to a secondary coil of the IMD to recharge a rechargeable power source of the IMD (810). This electromagnetic coupling is described in the foregoing embodiments as inductive coupling. However, other forms of electromagnetic coupling are possible within the scope of the current invention, such as RF coupling. In one embodiment, the current generated in a first coil has the same amplitude, frequency, and phase as that generated in the second coil.

It will be understood that the above-described embodiments are merely exemplary and many other embodiments are possible within the scope of the current invention. The coils may be carried by any one or more structures that are different from, or used in a different combination as compared to, the exemplary structures described herein. For instance, one coil may be carried on a garment and the second coil carried on a torso strap. As another example, a coil may be incorporated directly into the fabric of a chair, or even a seat of a car so that recharging may occur when a patient is seated is his car. In this latter case, a second structure such as a mechanism coupled to the car may suspend a second coil around the patient while the patient is driving.

As described herein, any types of coils known in the art are possible for use with the current invention. For instance, pancake coils or any other type of coils may be used. The coils may have any number of turns. Moreover, turns of the coils may be stacked one on top of another, and/or one or more turns may have a smaller circumference and reside inside or within one or more turns having a larger circumference. Turns of a coil may reside in a more angled configuration as shown in regards to coil 712 of FIG. 18, wherein a coil turn having a smaller circumference is not co-planer with a coil having a larger circumference. Thus, many types of coils and coil configurations are possible within the scope of the current invention.

It should also be appreciated that while the foregoing embodiments are most beneficially employed with an IMD that is implanted at a depth of greater than 3 cm and/or that has a secondary recharge coil that is angled within the body so that this coil is not parallel to adjacent surfaces of the patient's body, the techniques described herein may be used in other scenarios as well. For instance, they may likewise be employed for IMDs implanted closer to a cutaneous boundary and that have a secondary recharge coil that is substantially parallel to this cutaneous boundary. To this end, it should be understood that the IMD may be closer (and in some cases significantly so) to one coil as compared to the other coil, and need not be equally spaced between the coils. Thus, the description is to be considered illustrative only, with the scope of the invention to be determined by the Claims that follow.

What is claimed is:

1. A method, comprising:
   providing first and second primary coils adapted to be positioned external to a patient; and
   driving, via a control circuit, the first and second primary coils at a same time such that the first and the second primary coils are electromagnetically coupled to one another and to a secondary coil that is implantable within a patient.

2. The method of claim 1, wherein driving the first and second primary coils comprises generating a current in the first primary coil having substantially a same amplitude, phase, and frequency as a current generated in the second primary coil.

3. The method of claim 1, wherein driving the first and second primary coils comprises electrically coupling the first and second primary coils to one another in series.

4. The method of claim 1, wherein driving the first and second primary coils comprises driving the first and the second primary coils individually.

5. The method of claim 1, wherein positioning the first and second primary coils comprises positioning at least one of the first and second primary coils so that a respective major axis of at least one of the first and second primary coils intersects an implantable medical device that carries the secondary coil.

6. The method of claim 1, further comprising transferring energy from the first and second primary coils to the secondary coil via inductive coupling.

7. The method of claim 1, further comprising transferring energy from the first and second primary coils to the secondary coil via RF coupling.

8. The method of claim 1, further comprising powering at least one circuit of an implantable medical device via energy transferred from the first and second primary coils to the secondary coil.

9. The method of claim 8, wherein the at least one circuit is a circuit to deliver therapy to the patient.

10. The method of claim 1, further comprising recharging a rechargeable power source of an implantable medical device via energy transferred from the first and second primary coils to the secondary coil.

11. The method of claim 1, wherein positioning the second primary coil comprises positioning the second primary coil so that the secondary coil lies substantially between the first and second primary coils.

\* \* \* \* \*